United States Patent
Xu et al.

(10) Patent No.: US 9,328,083 B2
(45) Date of Patent: May 3, 2016

(54) 2-AMINATED METHYLENE OR 2-ESTERIFIED METHYLENE TANSHINONE DERIVATIVES, AND PREPARATION METHOD AND APPLICATION THEREOF

(71) Applicant: HANGZHOU BENSHENG PHARMACEUTICAL CO., LTD., Zhejiang (CN)

(72) Inventors: Rongzhen Xu, Zhejiang (CN); Frank Rong, Zhejiang (CN); Fuwen Xie, Fujian (CN); Hongxi Lai, Fujian (CN)

(73) Assignee: HANGZHOU BENSHENG PHARMACEUTICAL CO., LTD., Hangzhou (CN)

( * ) Notice: Subject to any disclaimer, the term of this patent is extended or adjusted under 35 U.S.C. 154(b) by 0 days.

(21) Appl. No.: 14/361,548

(22) PCT Filed: Nov. 30, 2012

(86) PCT No.: PCT/CN2012/085660
§ 371 (c)(1),
(2) Date: May 29, 2014

(87) PCT Pub. No.: WO2013/079022
PCT Pub. Date: Jun. 6, 2013

(65) Prior Publication Data
US 2015/0126552 A1 May 7, 2015

(30) Foreign Application Priority Data

Nov. 30, 2011 (WO) ................ PCT/CN2011/083261

(51) Int. Cl.
*C07D 307/77* (2006.01)
*C07D 405/12* (2006.01)

(52) U.S. Cl.
CPC ............ *C07D 307/77* (2013.01); *C07D 405/12* (2013.01)

(58) Field of Classification Search
None
See application file for complete search history.

(56) References Cited

FOREIGN PATENT DOCUMENTS

| CN | 1837200 A | 9/2006 |
|----|-----------|--------|
| CN | 101012270 A | 8/2007 |

OTHER PUBLICATIONS

Sun et al., 20(1) Yaoxue Xuebao 39-43 (1985) (CAS Abstract).*
Yang et al., 29(4) Zhongguo Yaoke Daxue Xuebao 255-258 (1998) (CAS Abstract).*
Chinese Applciation No. CN1837200 (CAS Abstract).*
International Preliminary Report on Patentability corresponding to International Patent Application No. PCT/CN2012/085660, issued Jun. 3, 2014.
Yang et al. 'Modification of Diterpenoid Quinones from Salvia miltiorrhiza'. Journal of China Pharmaceutical University. 1998, vol. 29, No. 4, pp. 255-258.
International Search Report for PCT/CN/2012/085660, dated Mar. 7, 2013 (4 pages).

* cited by examiner

*Primary Examiner* — Timothy R Rozof
(74) *Attorney, Agent, or Firm* — Lathrop & Gage LLP; Brian C. Trinque; Benjamin D. Heuberger

(57) ABSTRACT

The present invention belongs to the field of natural medicine and pharmaceutical chemistry, and specifically relates to novel 2-aminated methylene or 2-esterified methylene tanshinone I derivatives of formula (I) or a pharmaceutically acceptable salt thereof, to a process for the preparation of these compounds, compositions containing such compounds and their use in preparing antineoplastic medicaments. When X is nitrogen, formula I indicates 2-aminated methylene tanshinone I; when X is oxygen, formula I indicates 2-esterified methylene tanshinone I.

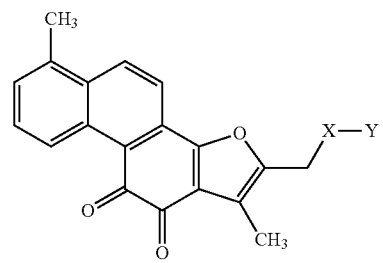

12 Claims, No Drawings

2-AMINATED METHYLENE OR 2-ESTERIFIED METHYLENE TANSHINONE DERIVATIVES, AND PREPARATION METHOD AND APPLICATION THEREOF

RELATED APPLICATIONS

This application is a 35 U.S.C. §371 filing of International Application No. PCT/CN2012/085660, filed Nov. 30, 2012, which claims priority to Chinese PCT No. PCT/CN2011/083261, filed Nov. 30, 2011, each of which is incorporated herein by reference in its entirety.

TECHNICAL FIELD

The present invention belongs to the field of natural medicine and pharmaceutical chemistry, and relates to novel tanshinone derivatives, in particular 2-aminated methylene or 2-esterified methylene tanshinone I derivatives, to a process for the preparation of these compounds, compositions containing such compounds and their use in preparing antineoplastic medicaments.

BACKGROUND OF THE INVENTION

Tanshinone I, also known as tanshinquinone I, has a chemical formula of 1,6-dimethyl-phenanthreno [1,2-b]furan-10,11-diketone and is extracted from the roots and stems of a Lamiaceae family plant, the *Salvia* miltiorrhiza Bge. Tanshinone I has various pharmacological effects and a wide range of clinical use. It can be used for the treatment of coronary heart disease, angina, myocardial infarction, viral myocarditis, cardiac arrhythmia, cerebral vascular disease, cerebral ischemia, cerebral thrombosis, cerebral infarction, hepatitis, tumor, hypertension and other diseases. Therefore, scientists have conducted a multitude of research on the following tanshinone derivatives.

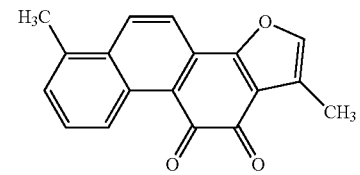

Tanshinone I

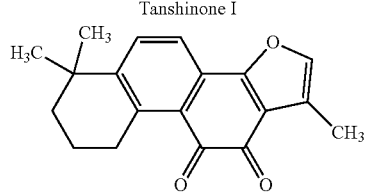

Tanshinone IIA

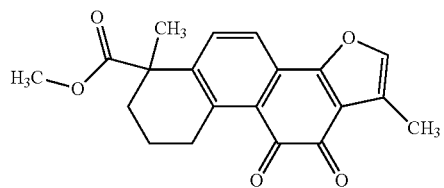

Methyl tanshinonate

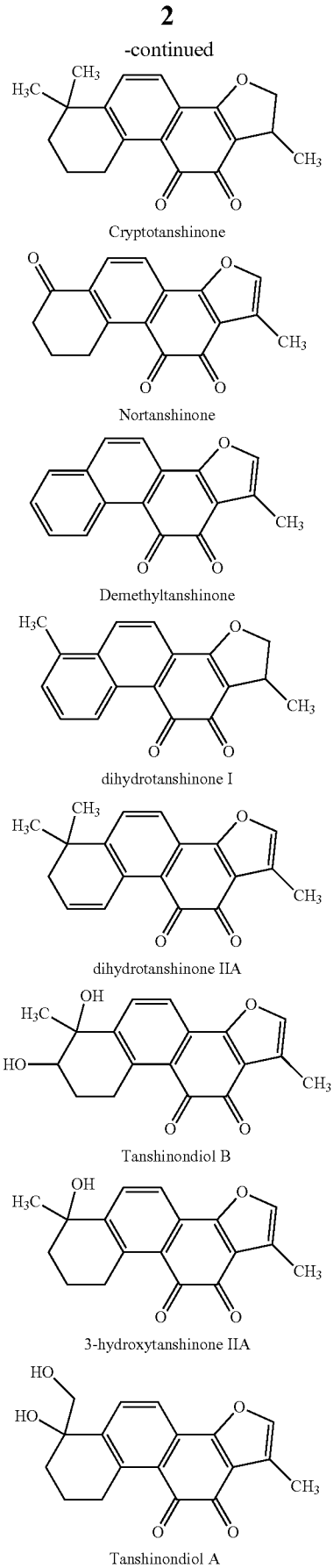

-continued

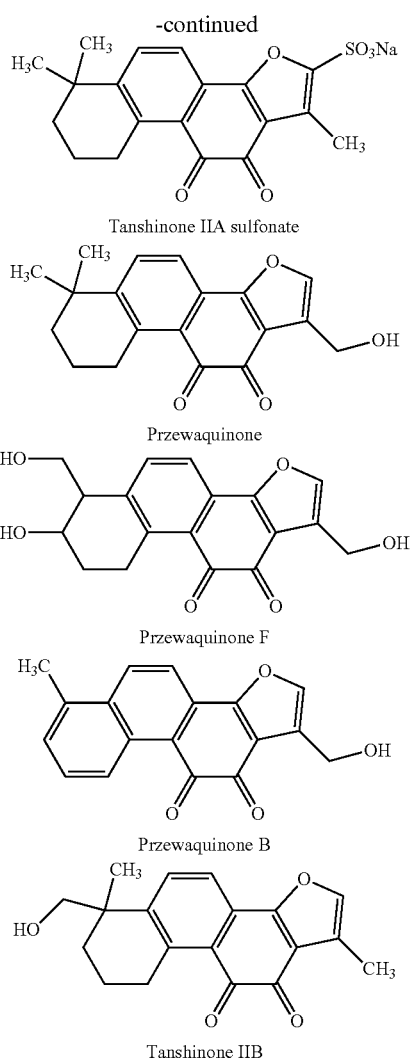

Tanshinone IIA sulfonate

Przewaquinone

Przewaquinone F

Przewaquinone B

Tanshinone IIB

Tanshinone I has poor solubility in water, and thus has low in vivo bioavailability. Therefore, scientists have attempted to modify the structure of tanshinone I in order to improve its water solubility and bioavailability so as to magnify the medicinal value of tanshinone I. (QIN Yinlin, Tanshinone I derivatives and applications thereof in pharmaceuticals, [P] CN 1837199A, 2006; QIN Yinlin, Tanshinone I derivatives and applications thereof in pharmaceuticals, [P] CN 1837200A, 2006; DU Zhiyun et al., Tanshinone derivatives and applications thereof in the preparation of a medicament for aldose reductase inhibitors, [P] CN 101012270A, 2007.)

Tanshinone I possesses certain antitumor effects. It is reported that, by observing the effects of tanshinone I on various indices of Hep G2 cells in in vitro and in vivo experiments, one can make an overall judgment whether it possesses anti-tumor effects. Results from the in vitro experiments indicate that tanshinone I can inhibit the proliferation of Hep G2 cells. In addition, results from the tumor inhibition experiments carried out on tumor-bearing nude mice indicate that tanshinone I can inhibit the tumor growth in the mice. That is, tanshinone I possesses antitumor effects in vivo as well. (ZHENG Guocan, L I Zhiying, Study on the inhibiting effect of Tanshinone I on HepG2 cell line in vitro, Modern Medical Journal, 2004, 32 (15): 296-298; ZHENG Guocan, L I Zhiying, Study on the anti-tumor effect and mechanism of tanshinone I, Journal of Practical Oncology, 2005, 20 (1): 33-35).

In addition, some studies have reported the effects of tanshinone I on the proliferation and apoptosis of SGC-7901 gastric adenocarcinoma cells in vitro. Experiments have found out that tanshinone I has significant inhibitory effect on the growth of the SGC-7901 human gastric adenocarcinoma cells cultured in vitro, and the inhibition of the cell growth is dependent on the concentration of tanshinone I within a certain range. (ZHOU Xiaoli et al., The effect of Tanshinone I on proliferation and apoptosis of human gastric adenocarcinoma cell line SGC-7901, Journal of Modern Oncology, 2011, 19 (3): 423-427.)

In spite of the multitude of studies on the structural modifications and bioactivity of tanshinone, reports on the synthesis and application of antitumor tanshinone compounds with good water solubility, low toxicity and excellent bioactivity have not yet been seen.

SUMMARY OF THE INVENTION

One object of the present invention is to provide novel tanshinone I derivatives characterized by formula (I), or a pharmaceutically acceptable salt thereof,

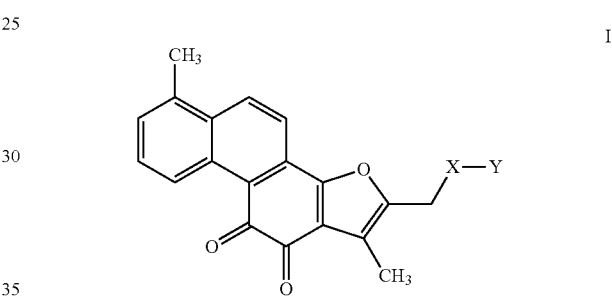

wherein X is nitrogen or oxygen;
when X is nitrogen, Y is ($R_1R_2$), leading to the compound of formula (I) being 2-aminated methylene tanshinone I of formula I-1; and when X is oxygen, Y is —(CO)R, leading to the compound of formula (I) being 2-esterified methylene tanshinone I of formula I-2,

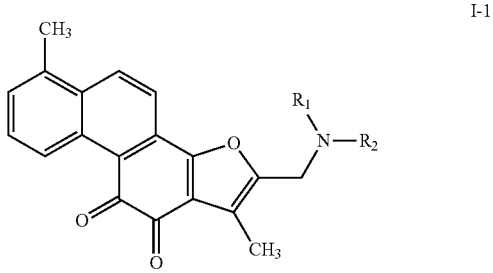

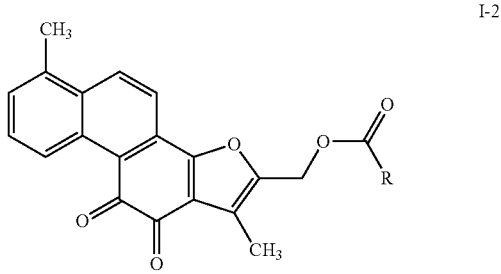

wherein R, $R_1$ and $R_2$ are selected from the group consisting of H, substituted or unsubstituted $C_1$-$C_{18}$ alkyl, substituted or unsubstituted $C_2$-$C_{18}$ alkenyl or alkynyl, substituted or unsubstituted $C_3$-$C_7$ cycloalkyl or cycloalkenyl, substituted or unsubstituted aryl, and substituted or unsubstituted heteroaryl or heterocyclyl, or $R_1$ and $R_2$ together with the carbon atoms to which they are attached form non-aromatic nitrogen-containing heterocyclyl or nitrogen-containing heteroaryl;

each of the aforementioned substituted group is substituted by one or more substituents selected from the group consisting of halogen, nitro, cyano, amino, hydroxyl, thiol, carboxyl, $C_1$-$C_6$ substituted amino, $C_1$-$C_6$ alkoxy, and $C_1$-$C_6$ alkylthio.

The second object of the present invention is to provide a process for preparing the 2-aminated methylene or 2-esterified methylene tanshinone I derivatives of formula (I) of the present invention:

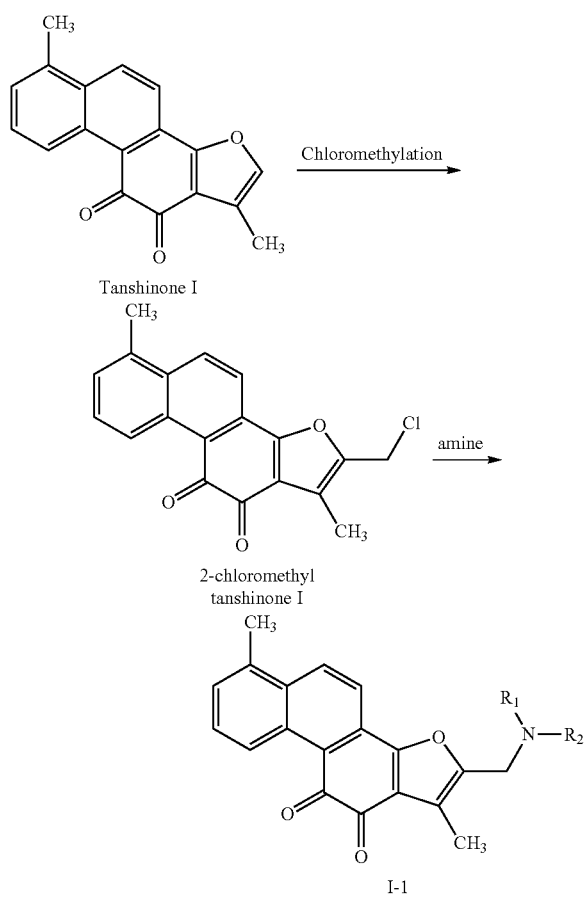

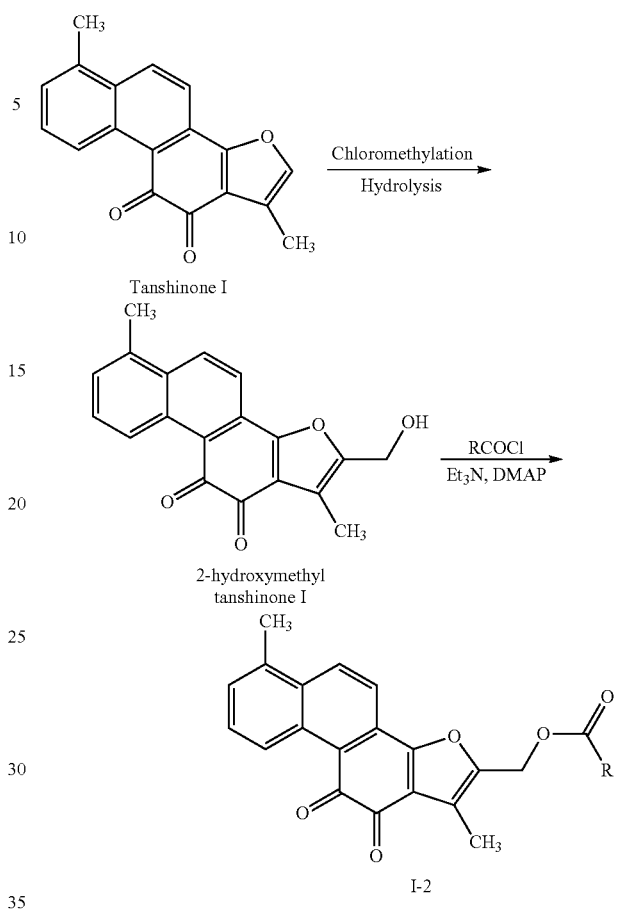

The 2-esterified methylene tanshinone I derivatives of formula (I-2) of the present invention can be prepared in a two-step reaction as shown above, comprising firstly subjecting tanshinone I (TA) to hydroxymethylation to produce a 2-hydroxymethyltanshinone I intermediate; then reacting the resulted 2-hydroxymethyltanshinone I with corresponding organic acyl chloride or anhydride in the presence of an alkali to produce a 2-esterified methylene tanshinone I of formula (I-2), wherein R is as defined above for formula (I); and optionally further subjecting the resulted compound to derivatization to produce other compounds of formula (I).

The third object of the present invention is to provide a pharmaceutical composition comprising the compound of the present invention, said pharmaceutical composition comprising at least one compound of the present invention and optionally a pharmaceutically acceptable excipient.

The fourth object of the present invention is to provide the use of the compound of the present invention or the pharmaceutical composition comprising the compound in the manufacture of a medicament, in particular an antitumor medicament. Correspondingly, the present invention provides a method for treating a subject suffering from tumor, comprising administrating to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer, and the like.

The 2-aminated methylene tanshinone I derivatives of formula (I-1) of the present invention can be prepared in a two-step reaction as shown above, comprising firstly subjecting tanshinone I (TA) to chloromethylation to produce a 2-chloromethylenetanshinone I intermediate; then reacting the resulted 2-chloromethylenetanshinone I with corresponding organic amine in the presence of an alkali to produce a 2-aminated methylene tanshinone I of formula (I-1), wherein $R_1$ and $R_2$ are as defined above for formula (I); and optionally further subjecting the resulted compound to derivatization to produce other compounds of formula (I).

The present invention also relates to the compounds of the present invention used for treating a tumor.

SPECIFIC EMBODIMENTS OF THE INVENTION

The present invention relates to a novel 2-aminated methylene or 2-esterified methylene tanshinone I derivative of formula (I), or a pharmaceutically acceptable salt thereof,

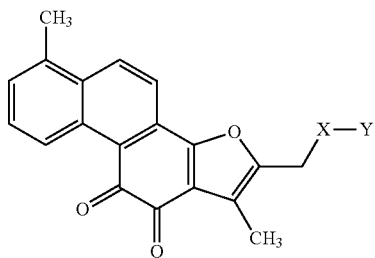

I wherein X is nitrogen or oxygen;

when X is nitrogen, Y is ($R_1R_2$), then the compound of formula (I) is 2-aminated methylene tanshinone I of formula I-1; and when X is oxygen, Y is —(CO)R, then the compound of formula (I) is 2-esterified methylene tanshinone I of formula I-2,

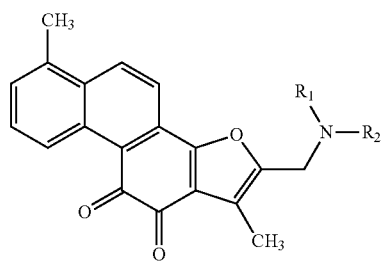

I-1

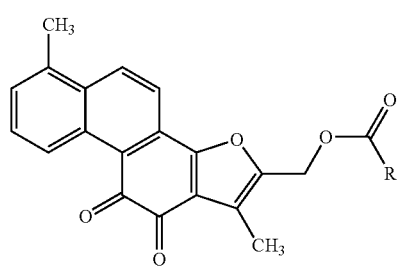

I-2 wherein R, $R_1$ and $R_2$ are selected from the group consisting of H, substituted or unsubstituted $C_1$-$C_{18}$ alkyl, substituted or unsubstituted $C_2$-$C_{18}$ alkenyl or alkynyl, substituted or unsubstituted $C_3$-$C_7$ cycloalkyl or cycloalkenyl, substituted or unsubstituted aryl, substituted or unsubstituted heteroaryl or heterocyclyl, or $R_1$ and $R_2$ together with the carbon atoms to which they are attached form a non-aromatic nitrogen-containing heterocyclyl or nitrogen-containing heteroaryl; each of the aforementioned substituted group is substituted by one or more substituents selected from the group consisting of halogen, nitro, cyano, amino, hydroxyl, thiol, carboxyl, $C_1$-$C_6$ substituted amino, $C_1$-$C_6$ alkoxy, and $C_1$-$C_6$ alkylthio.

According to a preferred embodiment of the present invention, X is nitrogen.

According to another preferred embodiment of the present invention, $R_1$ is H, methyl or ethyl; $R_2$ is $C_1$-$C_3$ alkyl substituted with a substituent selected from the group consisting of hydroxyl, $C_1$-$C_6$ alkylcarbonyloxy, cycloalkylcarbonyloxy, heterocyclyl carbonyloxy, amino-acid ester group wherein the amino is optionally substituted with $C_1$-$C_6$ alkoxycarbonyl, and $C_2$-$C_8$ dicarboxylic ester group optionally containing carbon-carbon double bond wherein one carboxyl is optionally esterified with $C_1$-$C_6$ alkyl.

According to a preferred embodiment of the present invention, $R_1$ is H or methyl; $R_2$ is ethyl substituted with said substituent.

According to another preferred embodiment of the present invention, said substituent is selected from the group consisting of hydroxyl, acetoxy, propionyloxy, butyryloxy, isobutyryloxy, valeryloxy, isovaleryloxy, tert-valeryloxy, piperidylcarbonyloxy, piperazinylcarbonyloxy, morpholinylcarbonyloxy, pyrrolidylcarbonyloxy, imidazolidinylcarbonyloxy, glycine ester group, N-tert-butoxycarbonyl glycine ester group, valine ester group, glutamic acid ester group, lysine ester group, malonic acid monoester group, succinic acid monoester group, maleic acid monoester group, methyl maleic acid ester group, glutaric acid monoester group, adipic acid monoester group, and pimelic acid monoester group.

According to a preferred embodiment of the present invention, the 2-aminated methylene tanshinone I is quaternized by a benzyl optionally substituted with halogen on the phenyl ring.

According to a preferred embodiment of the present invention, X is oxygen or sulfur, and R is $C_1$-$C_6$ alkyl optionally substituted with hydroxyl or halogen, or aryl or heteroaryl optionally substituted with hydroxyl or halogen.

Some preferred 2-aminated methylene or 2-esterified methylene tanshinone I derivatives according to the present invention is shown as below. These examples are only intended to further illustrate the present invention but not to make any restriction of the scope of the present invention.

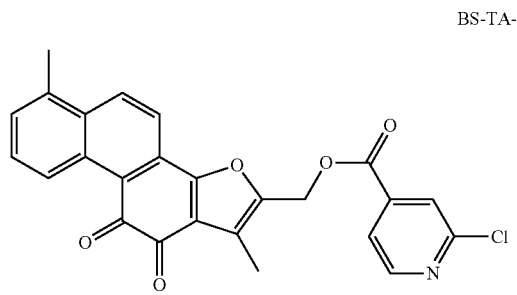

BS-TA-A01

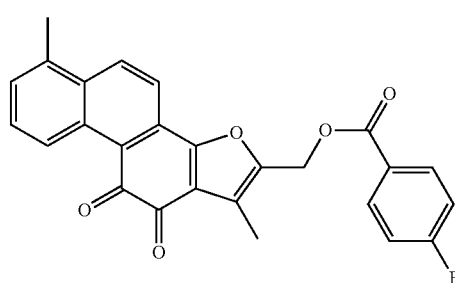

BS-TA-A02

BS-TA-A03
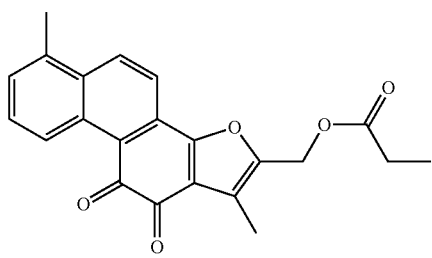
BS-TA-B08
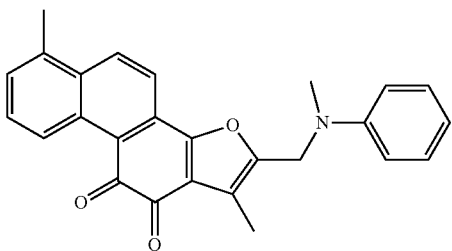
BS-TA-B01
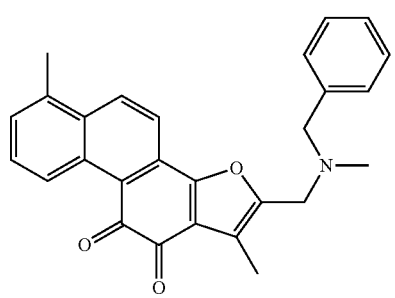
BS-TA-B09
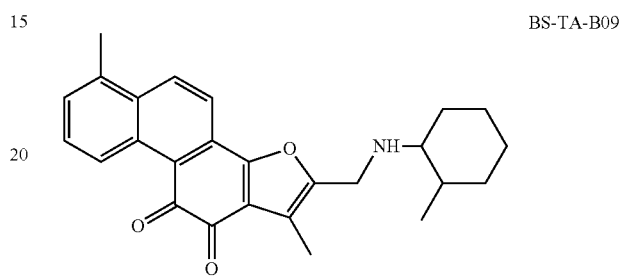
BS-TA-B03
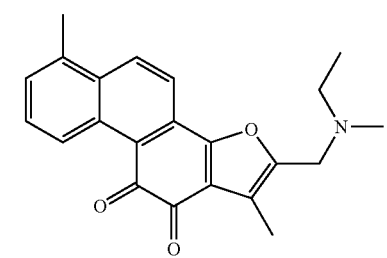
BS-TA-B10
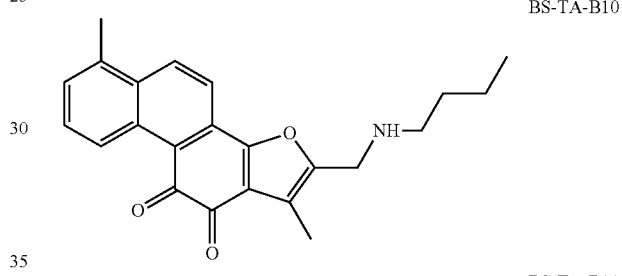
BS-TA-B05
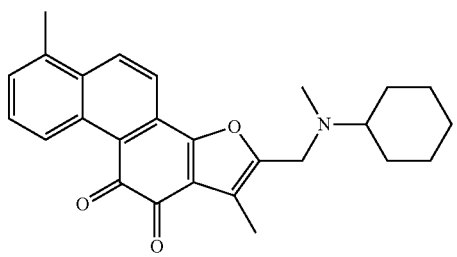
BS-TA-B11
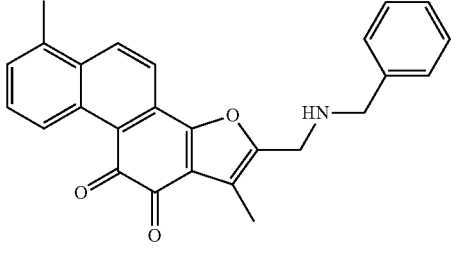
BS-TA-B06
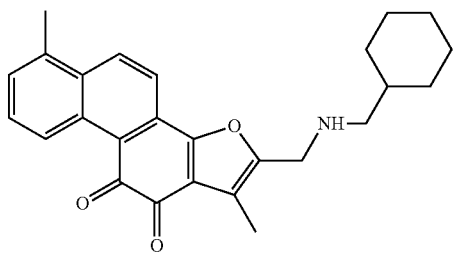
BS-TA-B12
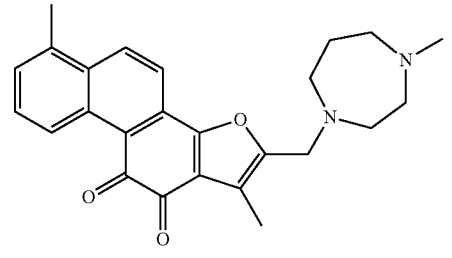
BS-TA-B07
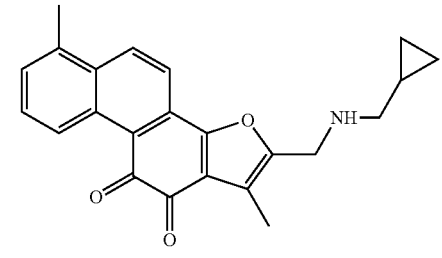
BS-TA-B13
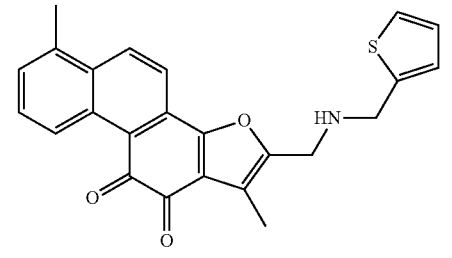

BS-TA-B14
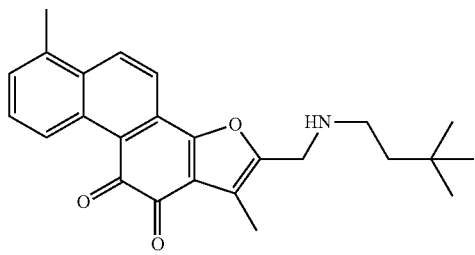
BS-TA-B16
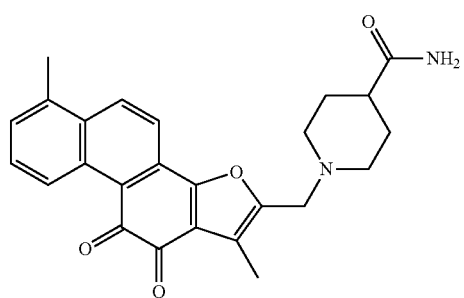
BS-TA-B17
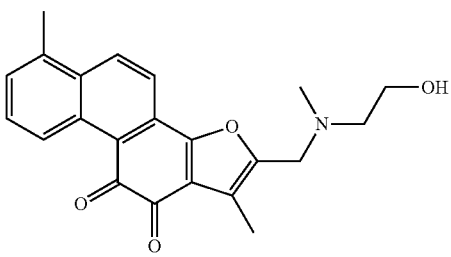
BS-TA-B18
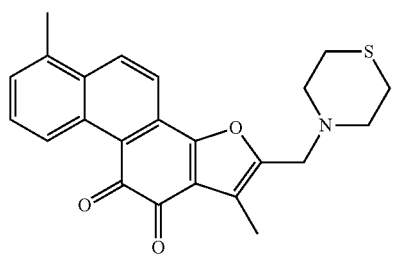
BS-TA-B21
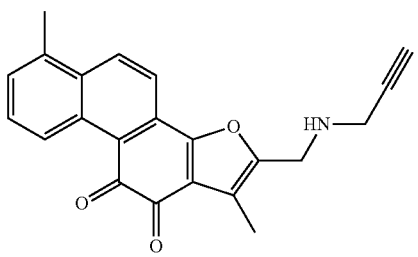
BS-TA-B22
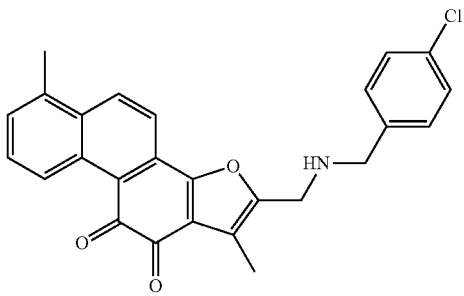
BS-TA-50
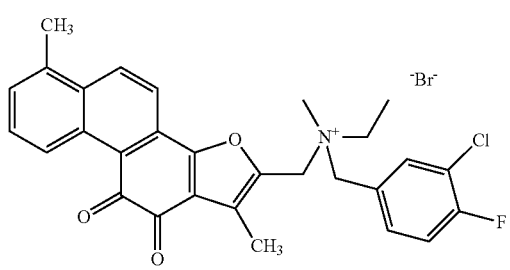
BS-TA-60
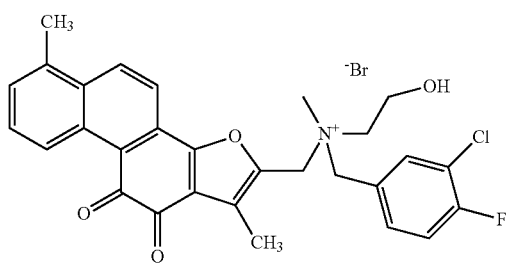
BS-TA-61
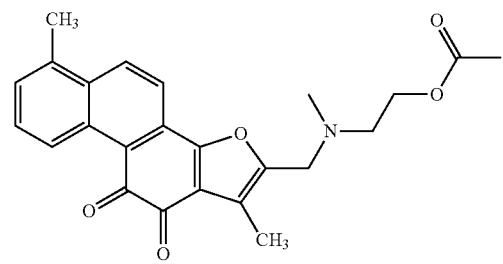
BS-TA-62
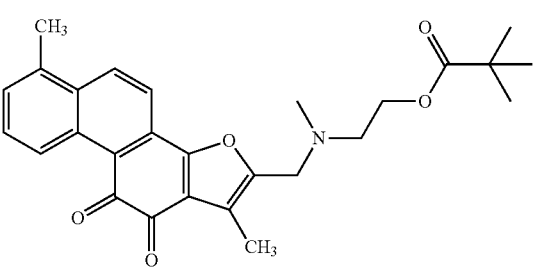

BS-TA-63
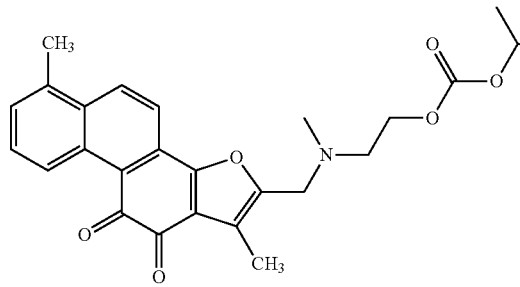
BS-TA-73
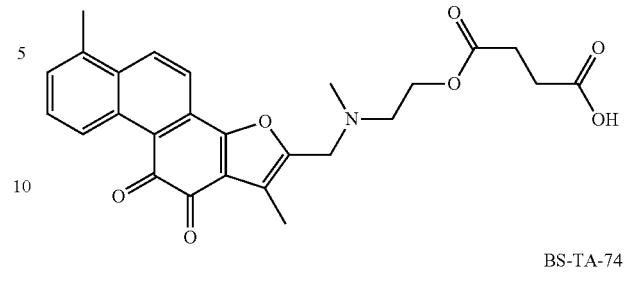
BS-TA-64
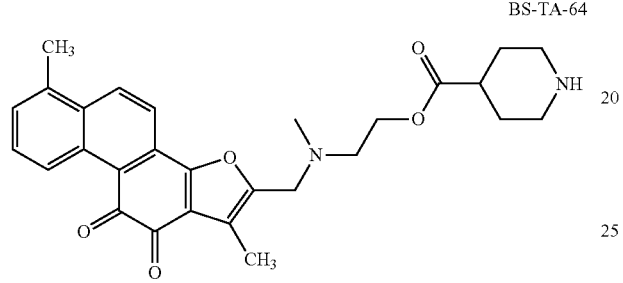
BS-TA-74
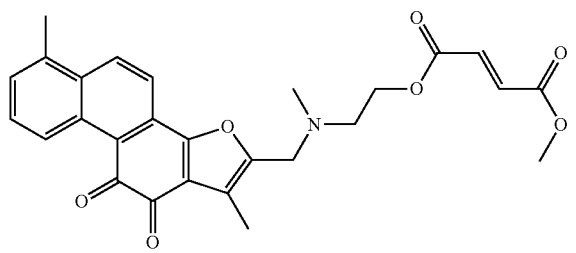
BS-TA-65
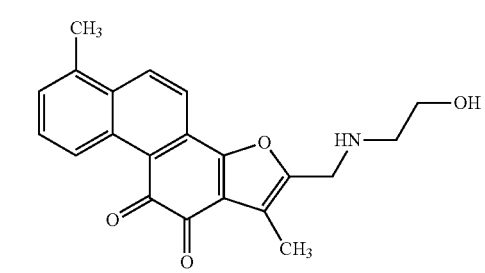
BS-TA-79
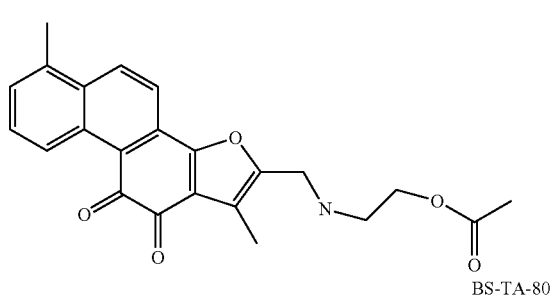
BS-TA-71
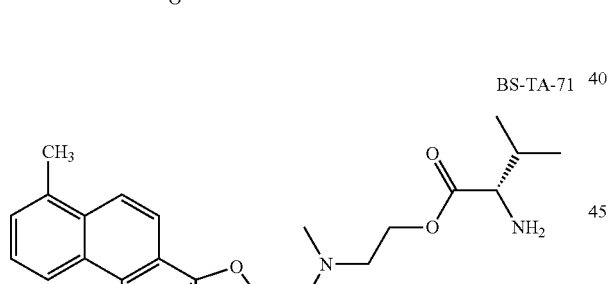
BS-TA-80
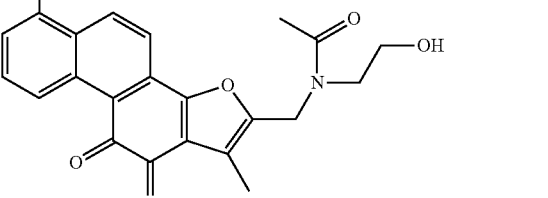
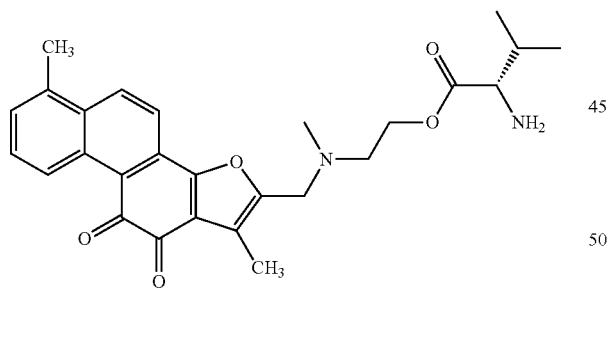
BS-TA-81
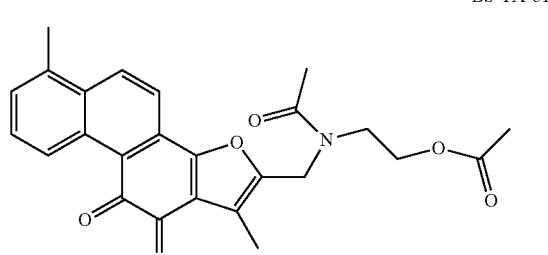
BS-TA-72
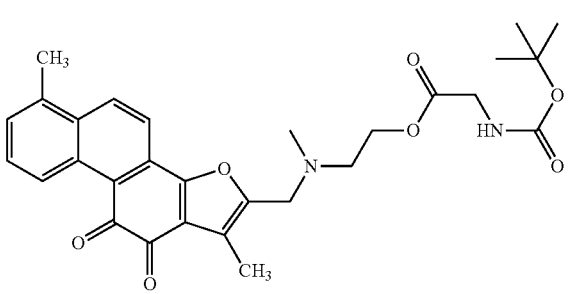
Some data for the above compounds are listed in the table below:
| Compound No. | Formula | Molecular Weight | Appearance | State | Total Yield (%) |
|---|---|---|---|---|---|
| BS-TA-A01 | $C_{25}H_{16}ClNO_5$ | 445.86 | Red | Solid | 4.8 |
| BS-TA-A02 | $C_{26}H_{17}FO_5$ | 428.42 | Red | Solid | 4.3 |
| BS-TA-A03 | $C_{22}H_{18}O_5$ | 362.39 | Red | Solid | 1.2 |

-continued

| Compound No. | Formula | Molecular Weight | Appearance | State | Total Yield (%) |
|---|---|---|---|---|---|
| BS-TA-B01 | $C_{27}H_{23}NO_3$ | 409.49 | Crimson | Solid | 20.0 |
| BS-TA-B03 | $C_{22}H_{21}NO_3$ | 347.42 | Brown | Solid | 26.4 |
| BS-TA-B05 | $C_{26}H_{27}NO_3$ | 401.51 | Crimson | Solid | 82.9 |
| BS-TA-B06 | $C_{26}H_{27}NO_3$ | 401.51 | Crimson | Solid | 57.6 |
| BS-TA-B07 | $C_{23}H_{21}NO_3$ | 359.43 | Crimson | Solid | 45.6 |
| BS-TA-B08 | $C_{26}H_{21}NO_3$ | 395.46 | Crimson | Solid | 98.5 |
| BS-TA-B09 | $C_{26}H_{27}NO_3$ | 401.51 | Red | Solid | 58.1 |
| BS-TA-B10 | $C_{23}H_{23}NO_3$ | 361.44 | Crimson | Solid | 51.7 |
| BS-TA-B11 | $C_{26}H_{21}NO_3$ | 395.46 | Crimson | Solid | 31.2 |
| BS-TA-B12 | $C_{25}H_{26}N_2O_3$ | 402.50 | Crimson | Solid | 23.9 |
| BS-TA-B13 | $C_{24}H_{19}NO_3S$ | 401.49 | Crimson | Solid | 46.9 |
| BS-TA-B14 | $C_{25}H_{27}NO_3$ | 389.50 | Crimson | Solid | 55.0 |
| BS-TA-B16 | $C_{25}H_{24}N_2O_4$ | 416.48 | Red | Solid | 80.1 |
| BS-TA-B17 | $C_{22}H_{21}NO_4$ | 363.42 | Crimson | Solid | 85.5 |
| BS-TA-B18 | $C_{23}H_{21}NO_3S$ | 391.49 | Crimson | Solid | 85.1 |
| BS-TA-B21 | $C_{22}H_{17}NO_3$ | 343.39 | Crimson | Solid | 25.1 |
| BS-TA-B22 | $C_{26}H_{20}ClNO_3$ | 429.91 | Crimson | Solid | 31.3 |
| BS-TA-50 | $C_{29}H_{26}BrClFNO_3$ | 570.88 | Green | Solid | 16.9 |
| BS-TA-60 | $C_{29}H_{26}BrClFNO_4$ | 586.88 | Red | Solid | 13.6 |
| BS-TA-61 | $C_{24}H_{23}NO_5$ | 405.44 | Brown | Solid | 31.5 |
| BS-TA-62 | $C_{27}H_{29}NO_5$ | 447.52 | Brown | Solid | 16.9 |
| BS-TA-63 | $C_{26}H_{27}NO_6$ | 449.5 | Brown | Solid | 22.6 |
| BS-TA-64 | $C_{28}H_{30}N_2O_5$ | 474.55 | Brown | Solid | 8.6 |
| BS-TA-65 | $C_{21}H_{19}NO_4$ | 349.38 | Brown | Solid | 32.2 |
| BS-TA-71 | $C_{27}H_{30}N_2O_5$ | 462.54 | Brown | Solid | 12.4 |
| BS-TA-72 | $C_{29}H_{32}N_2O_7$ | 520.57 | Brown | Solid | 22.2 |
| BS-TA-73 | $C_{26}H_{25}NO_7$ | 463.48 | Brown | Solid | 9.8 |
| BS-TA-74 | $C_{27}H_{25}NO_7$ | 475.49 | Brown | Solid | 57.7 |
| BS-TA-79 | $C_{23}H_{21}NO_5$ | 391.42 | Brown | Solid | 11.1 |
| BS-TA-80 | $C_{23}H_{21}NO_5$ | 391.42 | Brown | Solid | 2.8 |
| BS-TA-81 | $C_{25}H_{23}NO_6$ | 433.45 | Brown | Solid | 0.1 |

According to another embodiment of the present invention, the following compounds of formula (I) are particularly preferred:

BS-TA-B01

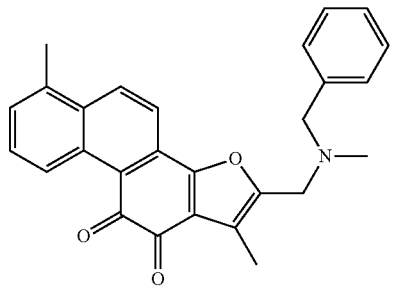

2-(N-methylbenzylamino)methyl-tanshinone I

BS-TA-B03

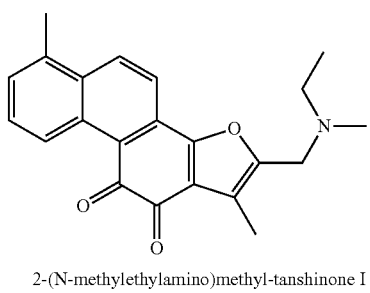

2-(N-methylethylamino)methyl-tanshinone I

BS-TA-B17

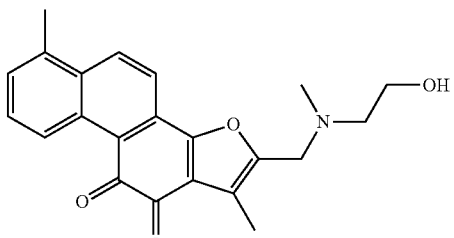

2-(N-methylethanolamino)methyl-tanshinone I

BS-TA-61

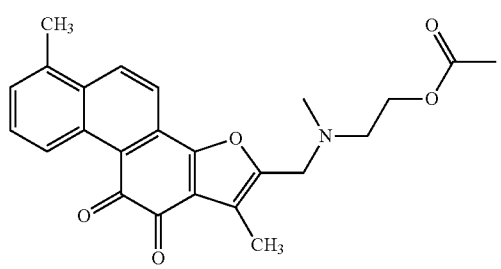

2-(N-methyl-acetoxyethyl-amino)methyl-tanshinone I

BS-TA-62

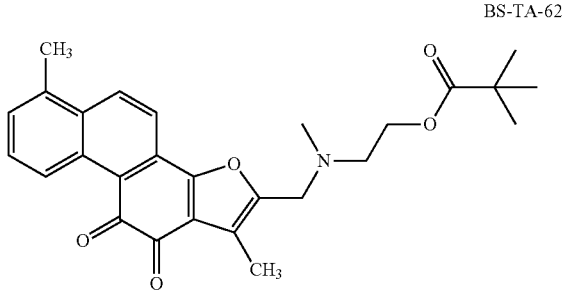

2-(N-methyl-t-butyryloxyethyl-amino)methyl-tanshinone I

BS-TA-64

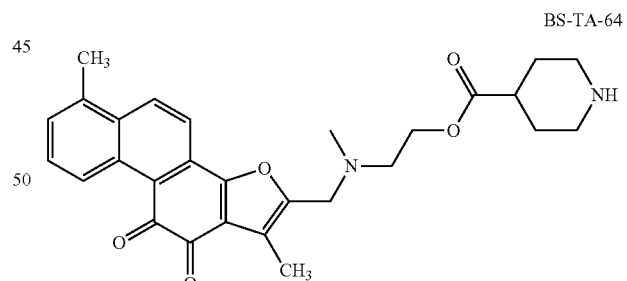

2-((N-methyl-(4-piperidylcarbonyl)oxyethyl-amino))methyl-tanshinone I

BS-TA-65

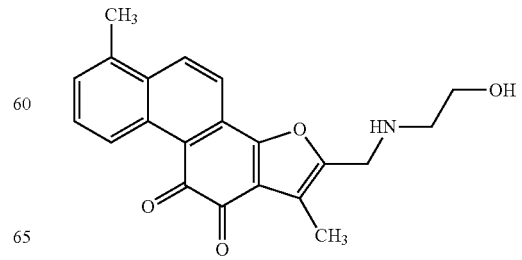

2-(ethanolamino)methyl-tanshinone I

-continued

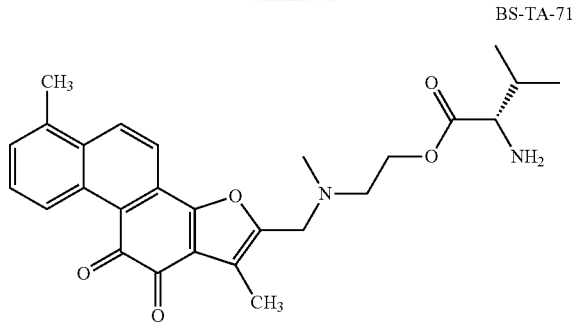

2-(N-methyl-L-valyloxyethylamino)methyl-tanshinone I

BS-TA-71

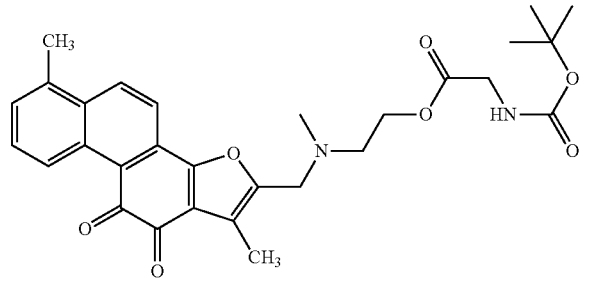

2-(N-methyl-Boc-glycyloxyethyl-amino)methyl-tanshinone I

BS-TA-72

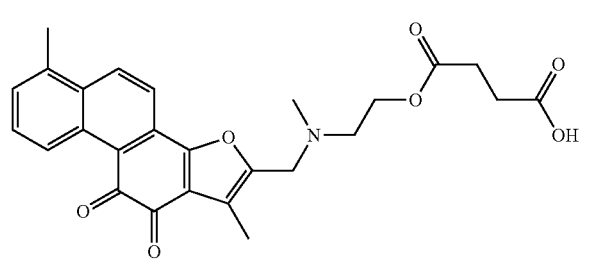

2-(N-methyl-monosuccinyloxyethyl-amino)methyl-tanshinone I

BS-TA-73

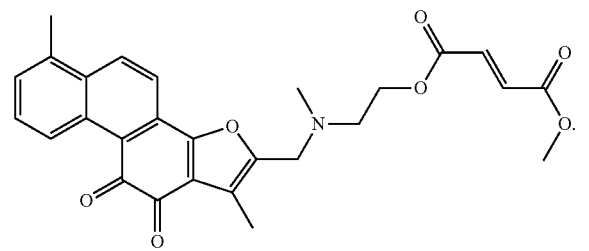

2-(N-methyl N-(methoxycarbonylacryloxyethyl)-amino)methyl-tanshinone I.

BS-TA-74

The 2-aminated methylene or 2-esterified methylene tanshinone I derivative of the present invention has an antitumor activity. As compared with tanshinone I per se, the preferred compounds of the present invention have an elevated antitumor activity, improved by several folds or even tens of folds.

As used herein, the term "alkyl" refers to a straight or branched hydrocarbon radical containing designated number of carbon atoms. The alkyl can comprise 1-18 carbon atoms, such as 1-12, 1-10, 1-8, 1-6, 1-5, 1-4 or 1-3 carbon atoms. Examples of the alkyl include, but not limited to, methyl, ethyl, n-propyl, isopropyl, tert-butyl, n-pentyl, n-hexyl and n-octadecyl.

The term "alkenyl" refers to a straight or branched alkenyl containing designated number of carbon atoms. The alkenyl can comprise 2-18 carbon atoms, such as 2-12, 2-10, 2-8, 2-6, 2-5, 2-4 or 2-3 carbon atoms. Examples of alkenyl include, but not limited to, vinyl, allyl and octadecenyl.

The term "$C_1$-$C_{18}$ alkylacyl" refers to a straight or branched alkylacyl containing 1-18 carbon atoms. Examples of $C_1$-$C_{18}$ alkylacyl include, but not limited to, acetyl and butyryl.

The term "$C_1$-$C_{18}$ alkoxycarbonyl" refers to a straight or branched alkoxycarbonyl containing 1-18 carbon atoms. Examples of $C_1$-$C_{18}$ alkoxycarbonyl include, but not limited to, methoxycarbonyl and tert-butoxycarbonyl.

The term "$C_1$-$C_{18}$ alkylthiocarbonyl" refers to a straight or branched alkylthiocarbonyl containing 1-18 carbon atoms. Examples of $C_1$-$C_{18}$ alkylthiocarbonyl include, but not limited to, methylthiocarbonyl and ethylthiocarbonyl.

The term "$C_3$-$C_7$ cycloalkyl or cycloalkenyl" refers to a saturated or unsaturated 3-7 membered monocyclic hydrocarbon radical. $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 (such as 6-12, and 6-10) carbon atoms. In the case of polycyclic aryl, at least one ring is aromatic. Aryl can also be one fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other can be aromatic or non-aromatic, with or without a heteroatom. Examples of heteroaryl include such as pyrrolyl, pyrazolyl, imidazolyl, oxazolyl, pyridyl, pyrimidinyl, furanyl, thienyl, isoxazolyl, indolyl, etc.

The term "nitrogen-containing heteroaryl" refers to a "heteroaryl" as defined above having at least one nitrogen atom as a ring member.

The term "heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclyl can be a monocyclic heterocyclyl having 4-8 ring atoms (such as 4-7 membered ring, 5-7 membered ring, 5-6 membered ring) or a bicyclic heterocyclyl having 7-11 ring atoms. A heterocyclyl can be aromatic or non-aromatic. Examples of heterocyclyls include azetidinyl, pyrrolidinyl, pyrrolinyl, tetrahydrofuranyl, dihydrofuranyl, piperazinyl, piperidinyl, morpholinyl, thiomorpholinyl, tetrahydropyranyl, tetrahydrothienyl, etc.

The term "nitrogen-containing heterocyclyl" refers to a "heterocyclyl" as defined above having at least one nitrogen atom as a ring member.

The term "halogen" refers to fluorine, chlorine, bromine or iodine.

The term "alkyl-substituted amino" refers to —N-alkyl.
The term "alkoxy" refers to —O-alkyl.
The term "alkylthio" refers to —S-alkyl.
The term "amino-acid ester group" refers to a group after the removal of the hydrogen atom from the carboxyl group of the amino acid.

The term "amino acid" refers to a group of small organic molecules having amino group on the α-carbon atom of carboxyl, preferably natural L-amino acids or their corresponding D-isomers. Examples of natural amino acids include alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid, etc.

As used herein, the term "pharmaceutically acceptable salts of the compounds of formula (I)" can be exemplified by the organic acid salts formed by an organic acid which comprises a pharmaceutically acceptable anion. These organic acid salts include, but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention can be prepared as follows.

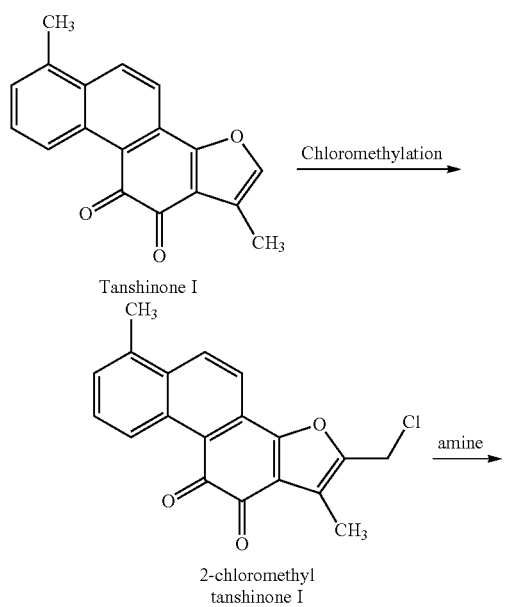

Tanshinone I 2-chloromethyl tanshinone I

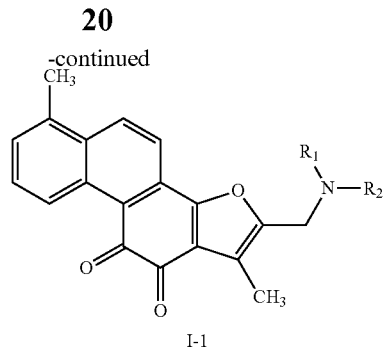

I-1

The 2-aminated methylene tanshinone I derivative of formula (I-1) of the present invention can be prepared by a two-step reaction as shown above, comprising firstly subjecting tanshinone I (TA) to chloromethylation to produce a 2-chloromethylenetanshinone I intermediate; then reacting the resulted 2-chloromethylene tanshinone I with corresponding organic amine in the presence of an alkali to produce a 2-aminated methylene tanshinone I of formula (I-1), wherein $R_1$ and $R_2$ are as defined in formula (I) above; and optionally further subjecting the resulted compound to derivatization to produce other compounds of formula (I).

The chloromethylation of tanshinone I (TA) is referred to as Blanc Reaction for chloromethylation, which is typically carried out under reduced or room temperature.

The above chloromethylation is typically carried out in the presence of an active chloromethylating agent. The chloromethylating agent herein can be, but not limited to, a mixture of paraformaldehyde and hydrochloric acid with zinc chloride (i.e. the conventional Blanc Reaction) or chloromethylmethyl ether.

The amination of 2-chloromethylenetanshinone I is typically carried out in the presence of an alkali.

The alkali herein can be, but not limited to, potassium carbonate and triethylamine.

The amination of 2-chloromethylenetanshinone I is typically carried out under reduced or room temperature. The reaction temperature depends on the activity of the organic amine.

The amination of 2-chloromethylenetanshinone I is typically carried out in a solvent. The solvent for the reaction can be, but not limited to, acetonitrile, tetrahydrofuran, N,N-dimethylformamide, dimethylsulfoxide (DMSO), etc.

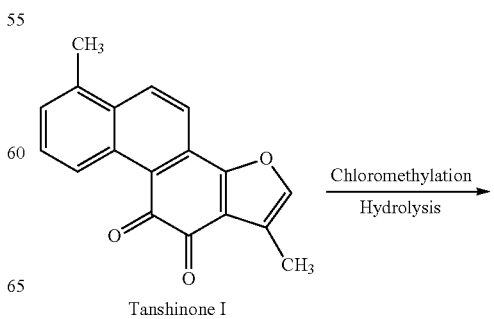

Tanshinone I

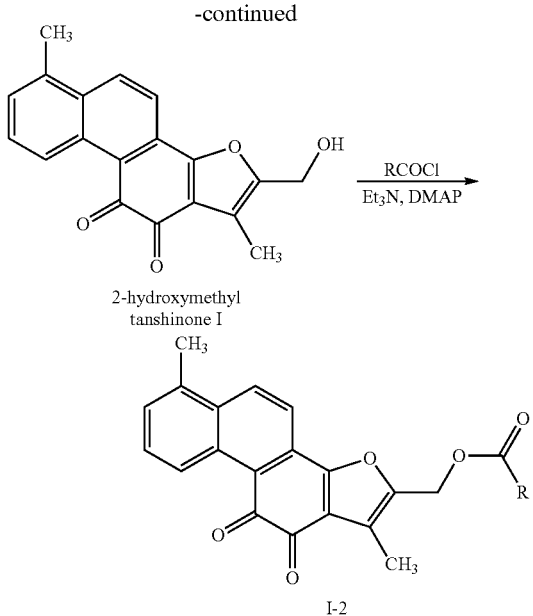

2-hydroxymethyl tanshinone I

↓ RCOCl, Et₃N, DMAP

I-2

As is shown in the above scheme, the 2-esterified methylene tanshinone I derivative of formula (I-2) of the present invention can be prepared by a two-step reaction, comprising firstly subjecting tanshinone I (TA) to hydroxymethylation to produce a 2-hydroxymethyltanshinone I intermediate; then reacting the resulted 2-hydroxymethyltanshinone I with corresponding organic acyl chloride or anhydride in the presence of an alkali to produce a 2-esterified methylene tanshinone I of formula (I-2), wherein R is as defined above for formula (I) above; and optionally further subjecting the resulted compound to derivatization to produce other compounds of formula (I).

Tanshinone I reacts with chloromethylmethyl ether in acetic acid as a solvent to produce a mixture of 2-chloromethyltanshinone I and 2-hydroxymethyltanshinone I, wherein the former can be hydrolyzed to produce the latter.

The esterification of 2-hydroxymethyltanshinone I is typically carried out in the presence of an alkali. The alkali herein can be, but not limited to, potassium carbonate, dimethylaminopyridine and triethylamine.

The esterification of 2-hydroxymethyltanshinone I is typically carried out at a temperature from 0° C. to 80° C. The reaction temperature depends on the reactivity of the organic acyl or anhydride.

The preparation of 2-aminated methylene or 2-esterified methylene tanshinone I derivative of formula (I) is typically operated as follows.

In the presence of hydrochloric acid and zinc chloride, natural tanshinone I obtained from extraction and separation and formaldehyde are subjected to Blanc Reaction for chloromethylation to produce a 2-chloromethyltanshinone I. The Blanc Reaction for chloromethylation is typically carried out under reduced or room temperature according to classical and mature operation procedures (C. C. Price, Org. React. 3, 1 (1946)).

2-Chloromethyltanshinone I is subjected to hydrolysis to produce the corresponding 2-hydroxymethyltanshinone I.

Tanshinone I reacts with chloromethylmethyl ether in an acetic acid solution at room temperature to produce a red solid mixture of 2-hydroxymethyltanshinone I and 2-chloromethyltanshinone I, wherein the latter can be hydrolyzed to produce the former.

The resulted 2-hydroxymethyltanshinone I reacts with corresponding organic acyl chloride in the presence of triethylamine and dimethylaminopyridine to produce a 2-esterified methylene tanshinone I. Alternatively, 2-chloromethyltanshinone I and a corresponding organic acid sodium salt can also produce the 2-esterified methylene tanshinone I by nucleophilic substitution in the presence of an alkali under heating in an organic solvent. Once the reaction terminates, the resulted product is extracted with an organic solvent, washed with water and saturated brine, dried and concentrated to produce a crude product, which is then separated by a silica-gel column or HPLC to give the pure product.

The resulted 2-chloromethyltanshinone I can also react with corresponding organic amine in the presence of an alkali at room temperature to produce a 2-aminated methylene tanshinone I. Once the reaction terminates, the resulted product is extracted with an organic solvent, washed with water and saturated brine, dried and concentrated to produce a crude product, which is then separated by a silica-gel column or HPLC to give the pure product.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis,* 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from being influenced in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

Specifically, among the preferred compounds of formula (I) of the present invention, BS-TA-A01 and BS-TA-A03 are prepared with extracted and separated natural tanshinone I (TA) as the starting material through hydroxymethylation and esterification.

BS-TA-B01, BS-TA-B03, BS-TA-B05, BS-TA-B06, BS-TA-B07, BS-TA-B08, BS-TA-B09, BS-TA-B10, BS-TA-B11, BS-TA-B12, BS-TA-B13, BS-TA-B14, BS-TA-B16, BS-TA-B17, BS-TA-B18, BS-TA-B21, BS-TA-B22 and BS-TA-65 are prepared with extracted and separated natural tanshinone I (TA) as the starting material through chloromethylation and amination.

BS-TA-50 and BS-TA-60 are obtained by quaternization of BS-TA-03 as the starting material.

BS-TA-61, BS-TA-62 and BS-TA-63 are obtained by esterification of BS-TA-17 as the starting material.

BS-TA-64, BS-TA-71, BS-TA-72 and BS-TA-74 are obtained by esterification of BS-TA-17 as the starting material followed by removal of the protection group.

BS-TA-73 is obtained by esterification of BS-TA-17 as the starting material.

BS-TA-79 is obtained by the Cbz-derivatization and esterification of BS-TA-65 as the starting material followed by the removal of Cbz.

BS-TA-80 is obtained by amidation of BS-TA-65 as the starting material.

BS-TA-81 is obtained by amidation and esterification of BS-TA-65 as the starting material.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. For example, description can be found in REMINGTON'S PHARMACEUTICAL SCIENCES, Martin, E. W., ed., Mack Publishing Company, 19th ed. (1995). Methods for preparing such pharmaceutical compositions include incorporation of other suitable pharmaceutical excipients, carriers, diluents, etc.

The pharmaceutical preparations of the present invention are produced by known methods, including conventional mixing, dissolving, or freeze drying processes.

The compounds of the present invention may be formulated into a pharmaceutical composition and administered to any subject in a route suitable for the selected administration manner, e.g., orally or parenterally (for example, by an intravenous, intramuscular, topical or subcutaneous route).

Thus, the present compounds may be systemically administered, e.g., orally administered, in combination with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredients (optionally encapsulated in liposomes), which are adapted for an extemporaneous preparation of sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceride, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 2-aminated methylene or 2-esterified methylene tanshinone I derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be prepared by a synthesis method known in the art.

EXAMPLE 1

Synthesis of Compound BS-TA-A03

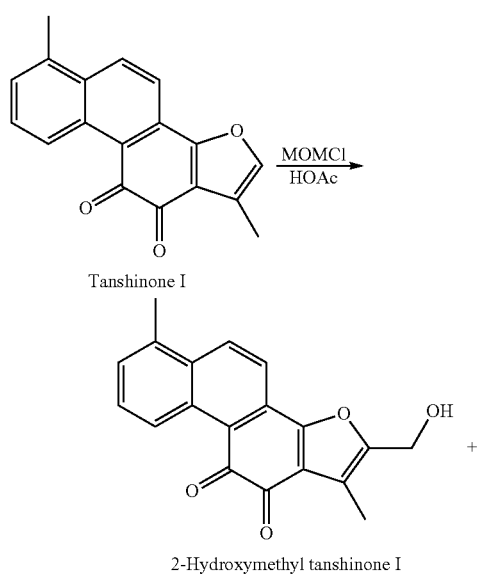

Tanshinone I

2-Hydroxymethyl tanshinone I

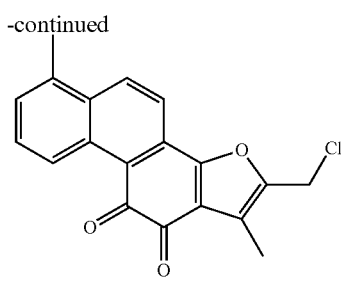

2-Chloromethyl tanshinone I wherein, MOMCl is chloromethylmethyl ether.

Chloromethylmethyl ether (1.6 g, 20 mmol) is added to an acetic acid solution (24 mL) of tanshinone I (0.276 g, 1 mmol) in an ice-bath. After the reaction solution is stirred for 20 hours at room temperature, the resulted precipitate is filtered. The residue is washed with water and dried to give a red solid, which is a mixture (0.2 g, yield 62%) of 2-hydroxymethyl-tanshinone I and 2-chloromethyltanshinone I, wherein the latter can be hydrolyzed to produce the former.

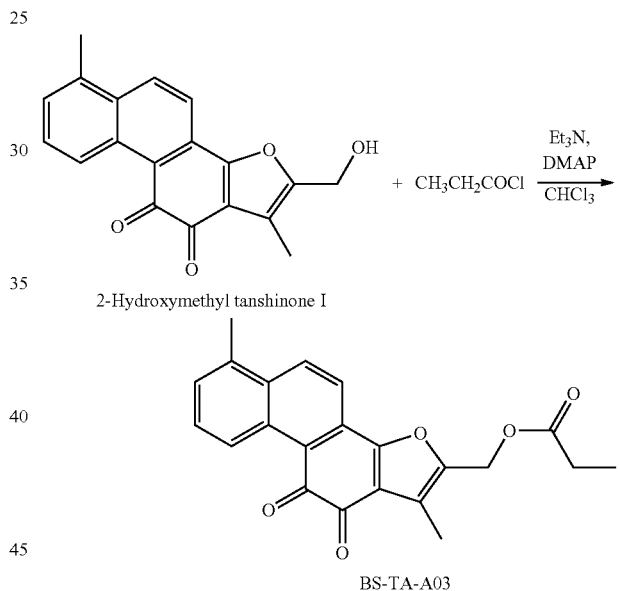

2-Hydroxymethyl tanshinone I

BS-TA-A03 wherein, Et$_3$N is triethylamine and DMAP is 4-dimethylaminopyridine.

At 0° C., propionyl chloride (20 mg, 0.216 mmol) is added dropwise to chloroform (3 mL) in which 2-hydroxymethyl-tanshinone I (50 mg, 0.18 mmol), triethylamine (41 mg, 0.45 mmol) and 4-dimethylaminopyridine (4 mg, 0.036 mmol) are dissolved. The reaction solution is then heated up to 65° C. and stirred overnight. Once the reaction terminates, water is added and the solution is subjected to extraction, separation and purification via silica-gel column or preparative chromatographic column to give the compound BS-TA-A03 (1.1 mg, yield 1.2%) as a red solid.

LC-MS: retention time: 4.2 min (83.13%); m/z: 363.3 (M+H).

$^1$H NMR (300 Hz, DMSO d-$_6$) δ 9.196 (d, 1H), 8.465 (d, 1H), 7.882 (d, 1H), 7.624 (m, 1H), 7.462 (d, 1H), 5.206 (s, 2H), 2.689 (s, 3H), 2.392 (m, 2H), 2.261 (s, 3H), 1.074 (m, 3H).

BS-TA-A01 is prepared according to the process for BS-TA-A03 using the same reagents as above by reacting the compound 2-hydroxymethyltanshinone I with 2-chloroisonicotinic acid.

LC-MS: retention time: 4.4 min (21.77%); m/z: 446.2 (M+H).

BS-TA-A02 is prepared according to the process for BS-TA-A03 using the same reagents as above by reacting the compound 2-hydroxymethyltanshinone I with p-fluorobenzoic acid.

LC-MS: retention time: 4.6 min (92.00%); m/z: 429.3 (M+H).

EXAMPLE 2

Synthesis of Compound BS-TA-B01

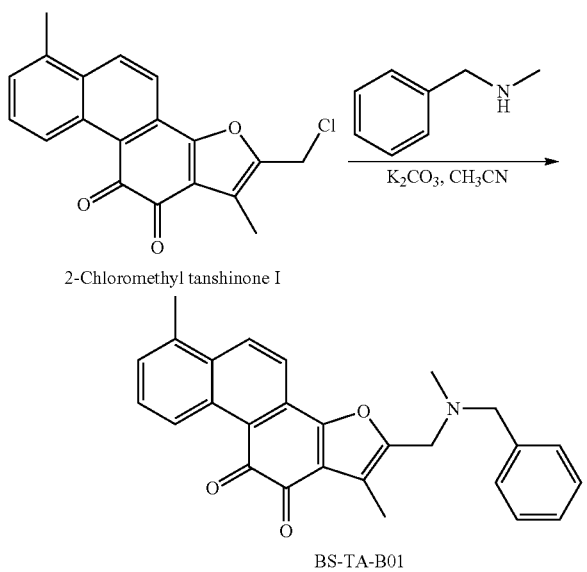

2-Chloromethyltanshinone I (50 mg, 0.18 mmol) is dissolved in dichloromethane (1 mL), to which an acetonitrile solution (3 mL) of N-methyl(phenyl)methylamine (47 mg, 0.54 mmol) as well as potassium carbonate (43 mg, 0.36 mmol) are added. The reaction solution is stirred for 3-5 hours at room temperature. Once the reaction terminates, the solution is subjected to extraction, followed by purification and separation via preparative thin layer chromatography to give the compound BS-TA-B01 (17.8 mg, yield 20.0%) as a crimson solid.

LC-MS: retention time: 3.2 min (92.29%); m/z: 410.2 (M+H).

$^1$H NMR (300 Hz, DMSO d-$_6$) δ 9.181 (d, 1H), 8.505 (d, 1H), 7.916 (d, 1H), 7.633 (m, 3H), 7.479 (m, 4H), 4.563 (s, 2H), 4.416 (s, 2H), 2.727 (s, 3H), 2.694 (s, 3H), 2.312 (s, 3H).

BS-TA-B03 is prepared according to the process for BS-TA-B01 using the same reagents as above by reacting the compound 2-hydroxymethyltanshinone I with N-methylethylamine.

LC-MS: retention time: 2.7 min (96.38%); m/z: 348.2 (M+H).

BS-TA-B05 is prepared according to the process for BS-TA-B01 using the same reagents as above by reacting the compound 2-hydroxymethyltanshinone I with N-methylcyclohexylamine.

LC-MS: retention time: 3.2 min (80.05%); m/z: 402.3 (M+H).

BS-TA-B06 is prepared according to the process for BS-TA-B01 using the same reagents as above by reacting the compound 2-hydroxymethyltanshinone I with cyclohexylmethylamine.

LC-MS: retention time: 3.3 min (85.49%); m/z: 402.4 (M+H).

BS-TA-B07 is prepared according to the process for BS-TA-B01 using the same reagents as above by reacting the compound 2-hydroxymethyltanshinone I with cyclopropanemethylamine.

LC-MS: retention time: 3.9 min (95.97%); m/z: 360.3 (M+H).

BS-TA-B08 is prepared according to the process for BS-TA-B01 using the same reagents as above by reacting the compound 2-hydroxymethyltanshinone I with N-methylaniline.

LC-MS: retention time: 4.7 min (91.40%); m/z: 396.3 (M+H).

BS-TA-B09 is prepared according to the process for BS-TA-B01 using the same reagents as above by reacting the compound 2-hydroxymethyltanshinone I with 2-methylcyclohexylamine.

LC-MS: retention time: 3.2 min (69.55%); m/z: 402.3 (M+H).

BS-TA-B10 is prepared according to the process for BS-TA-B01 using the same reagents as above by reacting the compound 2-hydroxymethyltanshinone I with butylamine.

LC-MS: retention time: 3.0 min (87.98%); m/z: 362.3 (M+H).

BS-TA-B11 is prepared according to the process for BS-TA-B01 using the same reagents as above by reacting the compound 2-hydroxymethyltanshinone I with benzylamine.

LC-MS: retention time: 4.2 min (82.78%); m/z: 396.3 (M+H).

BS-TA-B12 is prepared according to the process for BS-TA-B01 using the same reagents as above by reacting the compound 2-hydroxymethyltanshinone I with N-methylhomopiperazine.

LC-MS: retention time: 3.4 min (95.04%); m/z: 403.3 (M+H).

BS-TA-B13 is prepared according to the process for BS-TA-B01 using the same reagents as above by reacting the compound 2-hydroxymethyltanshinone I with 2-thienylmethylamine.

LC-MS: retention time: 4.2 min (99.54%); m/z: 402.3 (M+H).

BS-TA-B14 is prepared according to the process for BS-TA-B01 using the same reagents as above by reacting the compound 2-hydroxymethyltanshinone I with 2-thienylmethylamine.

LC-MS: retention time: 3.3 min (86.03%); m/z: 390.4 (M+H).

BS-TA-B16 is prepared according to the process for BS-TA-B01 using the same reagents as above by reacting the compound 2-hydroxymethyltanshinone I with 4-piperidylformamide LC-MS: retention time: 2.6 min (91.91%); m/z: 417.1 (M+H).

BS-TA-B17 is prepared according to the process for BS-TA-B01 using the same reagents as above by reacting the compound 2-hydroxymethyltanshinone I with N-methyl-2-hydroxyethylamine.

LC-MS: retention time: 2.0 min (94.23%); m/z: 364.2 (M+H).

BS-TA-B18 is prepared according to the process for BS-TA-B01 using the same reagents as above by reacting the compound 2-hydroxymethyltanshinone I with thiomorpholine.

LC-MS: retention time: 4.1 min (98.80%); m/z: 392.3 (M+H).

BS-TA-B21 is prepared according to the process for BS-TA-B01 using the same reagents as above by reacting the compound 2-hydroxymethyltanshinone I with allylamine.

LC-MS: retention time: 3.6 min (67.99%); m/z: 344.3 (M+H).

BS-TA-B22 is prepared according to the process for BS-TA-B01 using the same reagents as above by reacting the compound 2-hydroxymethyltanshinone I with p-chlorobenzylamine.

LC-MS: retention time: 4.4 min (76.49%); m/z: 430.3 (M+H).

EXAMPLE 3

Synthesis of Compound BS-TA-50

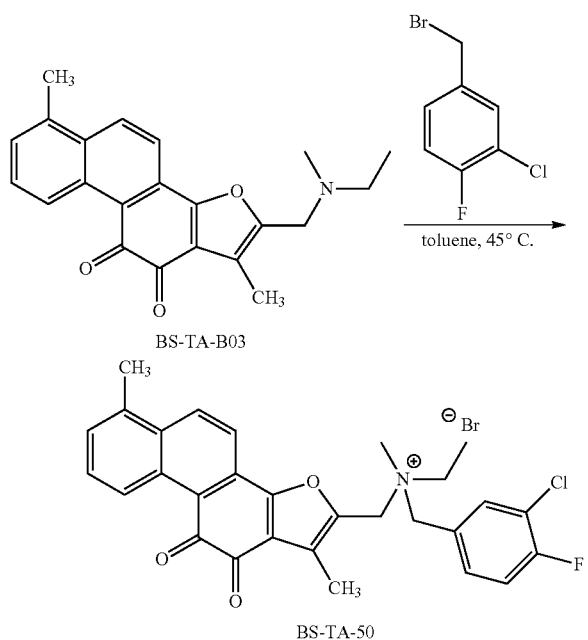

To a toluene solution (8 mL) of BS-TA-B03 (100 mg, 0.288 mmol) is added 4-(bromomethyl)-2-chloro-1-fluorobenzene (193 mg, 0.864 mmol). The reaction solution is heated up to 45° C. and stirred for 16 hours. Once the reaction completes, the resulted solid is filtered, and the residue is washed with toluene (5 mL*2) and dichloromethane (10 mL*2) to give the compound BS-TA-50 (28.06 mg, yield 16.9%) as a green solid.

LC-MS: retention time: 2.53 min (100%); m/z: 490 (M-Br);

$^1$H NMR (400 Hz, DMSO d-$_6$) δ 9.187 (d, J=8.8 Hz, 1H), 8.492 (d, J=8.8 Hz, 1H), 7.902 (t, 2H), 7.677-7.592 (m, 3H), 7.502 (d, J=6.8 Hz, 1H), 4.888 (d, J=14.8 Hz, 1H), 4.752 (d, J=14.8 Hz, 1H), 4.664 (s, 2H), 3.435 (m, 1H), 3.320 (m, 1H), 3.040 (s, 3H), 2.693 (s, 3H), 2.372 (s, 3H), 1.496 (t, 3H).

BS-TA-60 is prepared according to the process for BS-TA-50 using the same reagents as above by reacting the compound BS-TA-B17 with 4-(bromomethyl)-2-chloro-1-fluorobenzene.

LC-MS: retention time: 2.48 min (92.07%); m/z: 506 (M-Br).

$^1$H NMR (400 Hz, DMSO d-$_6$) δ 9.190 (d, J=8.4 Hz, 1H), 8.497 (d, J=8.4 Hz, 1H), 7.985-7.932 (m, 2H), 7.717-7.596 (m, 3H), 7.504 (d, J=6.8 Hz, 1H), 5.510 (s, 1H), 4.996 (d, J=14.8 Hz, 1H), 4.821 (t, 2H), 4.686 (d, J=14.8 Hz, 1H), 4.071 (s, 2H), 3.541 (m, 2H), 3.101 (s, 3H), 2.699 (s, 3H), 2.374 (s, 3H).

EXAMPLE 4

Synthesis of Compound BS-TA-61

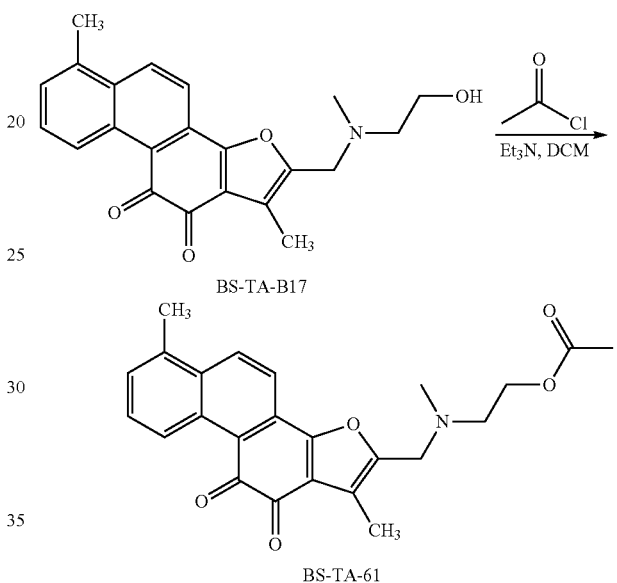

To dichloromethane (15 mL) are added BS-TA-B17 (200 mg, 0.55 mmol) and triethylamine (111.4 mg, 1.1 mmol), and then acetyl chloride (64.8 mg, 0.83 mmol) is added at 0° C. The reaction solution is allowed to warm up to room temperature and stirred for 1.5 hours. Once the reaction completes, a drop of water is added and the solvent is removed. The resulted crude product is separated and purified via preparative thin layer chromatography (dichloromethane/ethyl acetate 2:1) to give the compound BS-TA-61 (53.34 mg, yield 31.5%) as a brown solid.

LC-MS: retention time: 2.1 min (98.00%); m/z: 406.2 (M+H).

$^1$H NMR (400 Hz, DMSO d-$_6$) δ 9.164 (d, J=8.8 Hz, 1H), 8.448 (d, J=8.4 Hz, 1H), 7.853 (d, J=8.8 Hz, 1H), 7.607 (t, 1H), 7.442 (d, J=6.0 Hz, 1H), 4.158 (s, 2H), 3.698 (s, 2H), 2.681 (s, 5H), 2.276 (s, 3H), 2.212 (s, 3H), 2.010 (s, 3H).

BS-TA-62 is prepared according to the process for BS-TA-61 using the same reagents as above by reacting the compound BS-TA-B17 with pivaloyl chloride.

LC-MS: retention time: 2.4 min (100.0%); m/z: 448.3 (M+H).

$^1$H NMR (400 Hz, CDCl$_3$) δ 9.268 (d, J=8.8 Hz, 1H), 8.312 (d, J=8.8 Hz, 1H), 7.874 (d, J=8.8 Hz, 1H), 7.567 (t, 1H), 7.367 (d, J=7.2 Hz, 1H), 4.277 (s, 2H), 3.689 (s, 2H), 2.790 (s, 2H), 2.708 (s, 3H), 2.398 (s, 3H), 2.298 (s, 3H), 1.212 (s, 9H).

BS-TA-63 is prepared according to the process for BS-TA-61 using the same reagents as above by reacting the compound BS-TA-B17 with isopropyl chloroformate.

LC-MS: retention time: 2.3 min (100.0%); m/z: 450.3 (M+H).

$^1$H NMR (400 Hz, CDCl$_3$) δ 9.268 (d, J=8.8 Hz, 1H), 8.312 (d, J=8.4 Hz, 1H), 7.874 (d, J=8.0 Hz, 1H), 7.565 (t, 1H), 7.367 (d, J=6.8 Hz, 1H), 4.882 (m, 1H), 4.298 (s, 2H), 3.707 (s, 2H), 2.946 (s, 1H), 2.818 (s, 1H), 2.707 (s, 3H), 2.401 (s, 3H), 2.294 (s, 3H), 1.295 (d, 6H).

EXAMPLE 5

Synthesis of Compound BS-TA-64

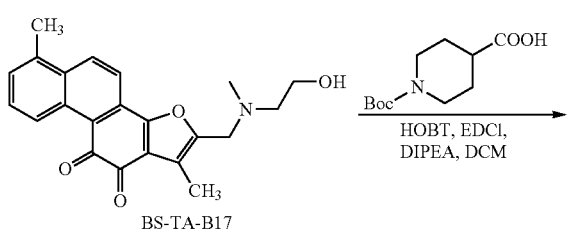

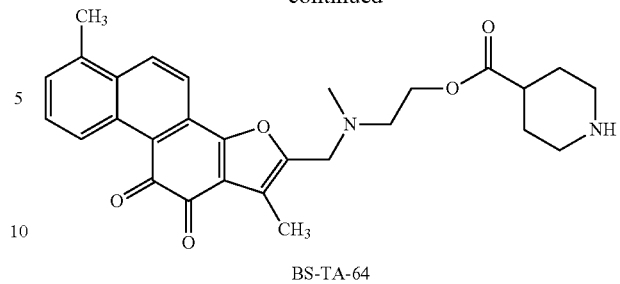

wherein, TFA represents trifluoroacetic acid.

To dichloromethane (6 mL) is added BS-TA-64-1 (45 mg, 0.078 mmol), followed by trifluoroacetic acid (3 mL). The reaction solution is stirred for 2 hours at room temperature. Once the reaction completes, the reaction solution is concentrated and adjusted to pH 9 with saturated sodium bicarbonate solution. The organic phase resulted from the extraction of the reaction solution is separated and purified via preparative thin layer chromatography to give the compound BS-TA-64 (22.41 mg, yield 60.6%) as a brown solid.

LC-MS: retention time: 2.0 min (100.0%); m/z: 475.3 (M+H).

$^1$H NMR (400 Hz, DMSO d-$_6$) δ 9.140 (d, J=9.2 Hz, 1H), 8.405 (d, J=6.4 Hz, 1H), 7.808 (d, J=7.6 Hz, 1H), 7.587 (t, 1H), 7.426 (d, J=6.8 Hz, 1H), 4.165 (s, 2H), 3.664 (s, 2H), 2.818 (d, J=12.0 Hz, 2H), 2.665 (s, 5H), 2.415-2.278 (m, 3H), 2.235 (s, 3H), 2.196 (s, 3H), 2.115 (m, 1H), 1.677 (d, J=12.0 Hz, 2H), 1.427-1.341 (m, 2H).

wherein HOBT is 1-hydroxybenzotriazole, EDCl is 1-ethyl-(3-dimethylaminopropyl)carbodiimide hydrochloride, and DIPEA is N,N-diisopropylethylamine.

To dichloromethane (15 mL) are added BS-TA-B17 (200 mg, 0.55 mmol), 1-Boc-4-piperidylcarboxylic acid (151.4 mg, 0.66 mmol), 1-hydroxybenzotriazole (148.6 mg, 1.1 mmol), 1-ethyl-(3-dimethylaminopropyl) carbodiimide hydrochloride (210.9 mg, 1.1 mmol) and N,N-diisopropylethylamine (177.1 mg, 1.375 mmol). The reaction solution is stirred for 48 hours at room temperature. Once the reaction completes, the solvent is removed. The resulted crude product is separated and purified via preparative thin layer chromatography (dichloromethane/ethyl acetate 1:2) to give the compound BS-TA-64-1 (45 mg, yield 14.25%) as a brown solid.

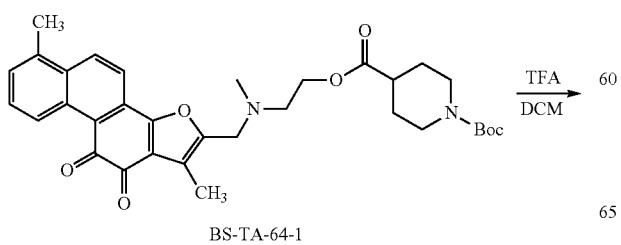

EXAMPLE 6

Synthesis of Compound BS-TA-65

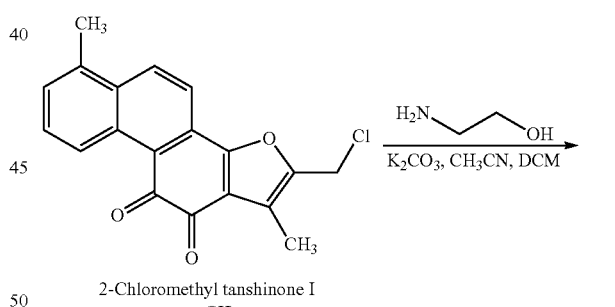

To dichloromethane (10 mL) is added 2-chloromethyl tanshinone I (100 mg, 0.309 mmol), followed by an acetonitrile solution (15 mL) of ethanolamine (56.4 mg, 0.926 mmol) and potassium carbonate (127.6 mg, 0.926 mmol). After the reaction solution is stirred for 2 hours at room temperature, the resulted product is filtered. The residue is washed with water (10 mL*2) and dichloromethane (5 mL*2) to give the compound BS-TA-65 (27.21 mg, yield 32.2%) as a brown solid.

LC-MS: retention time: 2.0 min (97.46%); m/z: 350.2 (M+H).

$^1$H NMR (400 Hz, DMSO d-$_6$) δ 9.148 (d, J=7.6 Hz, 1H), 8.418 (s, 1H), 7.863 (d, J=8.4 Hz, 1H), 7.579 (m, 1H), 7.434 (s, 1H), 4.525 (s, 1H), 3.790 (s, 2H), 3.482 (s, 2H), 2.671-2.628 (m, 5H), 2.194-2.156 (m, 4H).

EXAMPLE 7

Synthesis of Compound BS-TA-71

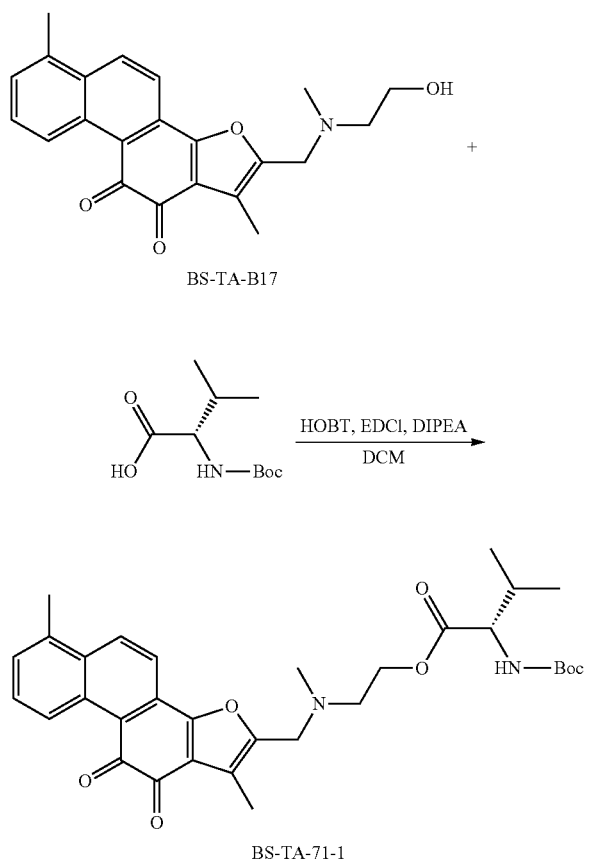

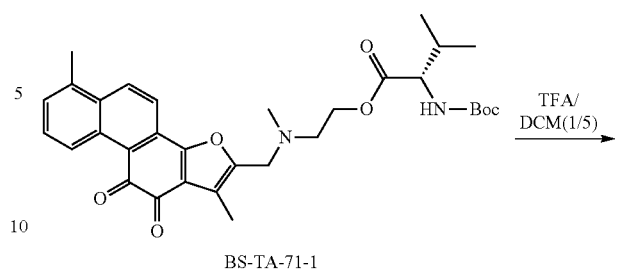

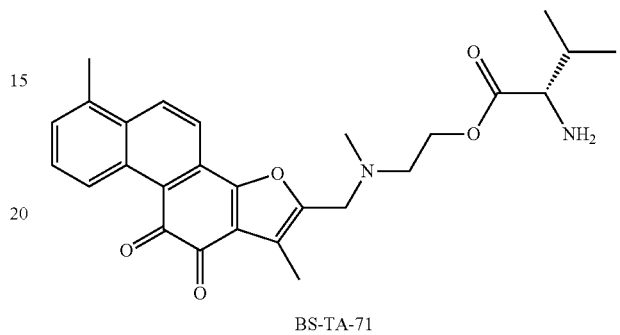

To dichloromethane (10 mL) are added BS-TA-B17 (150 mg, 0.413 mmol), 1-hydroxybenzotriazole (111 mg, 0.826 mmol), 1-ethyl-(3-dimethylaminopropyl)carbodiimide hydrochloride (157 mg, 0.826 mmol) and N,N-diisopropylethylamine (133 mg, 1.033 mmol), followed by Boc-L-valine (107 mg, 0.496 mmol). The reaction solution is stirred for 1 hour at room temperature. Once the reaction completes, water (10 mL) is added and dichloromethane (50 mL) is used for extraction. The crude product resulted from concentrating the organic phase is separated and purified via preparative thin layer chromatography (dichloromethane/ethyl acetate 1:1) to give the compound BS-TA-71-1 (70 mg, yield 30.2%) as a brown solid.

The compound BS-TA-71-1 (70 mg, 0.125 mmol) is dissolved in a mixed solution of trifluoroacetic acid (2 mL) and dichloromethane (10 mL). The reaction solution is stirred for 3 hours at room temperature. Once the reaction completes, the solvent is removed. The resulted crude product is separated and purified via preparative thin layer chromatography to give the compound BS-TA-71 (24 mg, yield 41.7%) as a brown solid.

LC-MS: retention time: 2.8 min (96.28%); m/z: 463.2 (M+H).

$^1$H NMR (400 Hz, CDCl$_3$) δ 9.25 (d, J=8.8 Hz, 1H), 8.30 (d, J=8.8 Hz, 1H), 7.85 (d, J=8.8 Hz, 1H), 7.55 (t, 1H), 7.36 (d, J=6.8 Hz, 1H), 4.33 (t, 2H), 3.72 (s, 2H), 3.37 (d, J=4.8 Hz, 1H), 2.82 (t, 2H), 2.70 (s, 3H), 2.41 (s, 3H), 2.30 (s, 3H), 2.19 (s, 1H), 0.99 (d, J=6.8 Hz, 3H), 0.92 (d, J=6.8 Hz, 3H).

EXAMPLE 8

Synthesis of Compound BS-TA-72

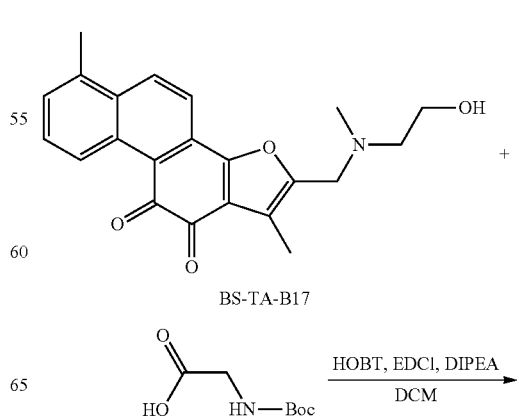

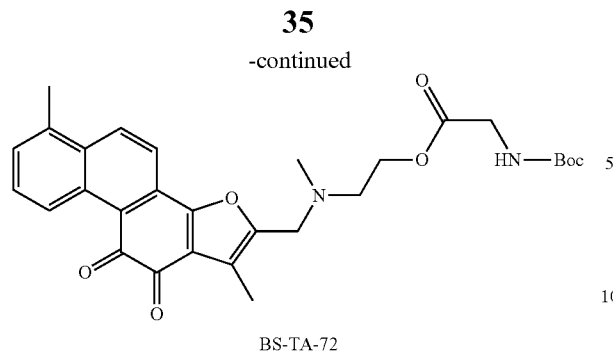

BS-TA-72

To dichloromethane (10 mL) are added BS-TA-B17 (200 mg, 0.550 mmol), 1-hydroxybenzotriazole (149 mg, 1.10 mmol), 1-ethyl-(3-dimethylaminopropyl)carbodiimide hydrochloride (211 mg, 1.10 mmol) and N,N-diisopropylethylamine (178 mg, 1.38 mmol), followed by Boc-glycine (145 mg, 0.66 mmol). The reaction solution is stirred for 30 minutes at room temperature. Once the reaction completes, water (10 mL) is added and dichloromethane (50 mL) is used for extraction. The crude product resulted from concentrating the organic phase is separated and purified via preparative thin layer chromatography (dichloromethane/ethyl acetate 1:1) and preparative chromatography to give the compound BS-TA-72 (25 mg, yield 22.2%) as a brown solid.

LC-MS: retention time: 2.0 min (100%); m/z: 521.2 (M+H).

$^1$H NMR (400 Hz, CDCl$_3$) δ 9.26 (d, J=9.2 Hz, 1H), 8.32 (d, J=8.8 Hz, 1H), 7.86 (d, J=8.4 Hz, 1H), 7.56 (t, 1H), 7.36 (d, J=6.8 Hz, 1H), 5.01 (s, 1H), 4.35 (t, 2H), 3.95 (d, J=5.2 Hz, 2H), 3.70 (s, 2H), 2.80 (m, 2H), 2.70 (s, 3H), 2.39 (s, 3H), 2.29 (s, 3H), 1.44 (s, 9H).

BS-TA-74 is prepared according to the process for BS-TA-72 using the same reagents as above by reacting the compound BS-TA-B17 with monomethyl fumarate.

LC-MS: retention time: 2.3 min (96.87%); m/z: 476.3 (M+H).

$^1$H NMR (400 Hz, CDCl$_3$) δ 9.25 (d, J=9.2 Hz, 1H), 8.29 (d, J=8.8 Hz, 1H), 7.83 (d, J=8.8 Hz, 1H), 7.56 (t, 1H), 7.35 (d, J=6.8 Hz, 1H), 6.86 (s, 2H), 4.38 (t, 2H), 3.74 (s, 3H), 3.68 (s, 2H), 2.82 (t, 2H), 2.70 (s, 3H), 2.41 (s, 3H), 2.28 (s, 3H).

EXAMPLE 9

Synthesis of Compound BS-TA-73

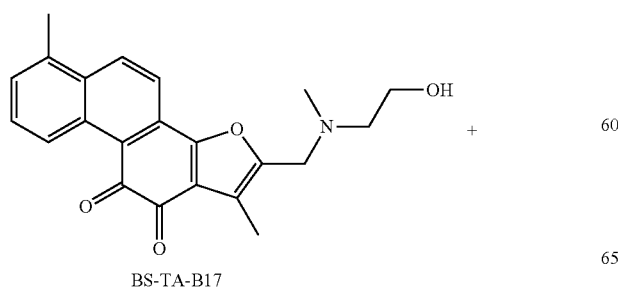

BS-TA-B17

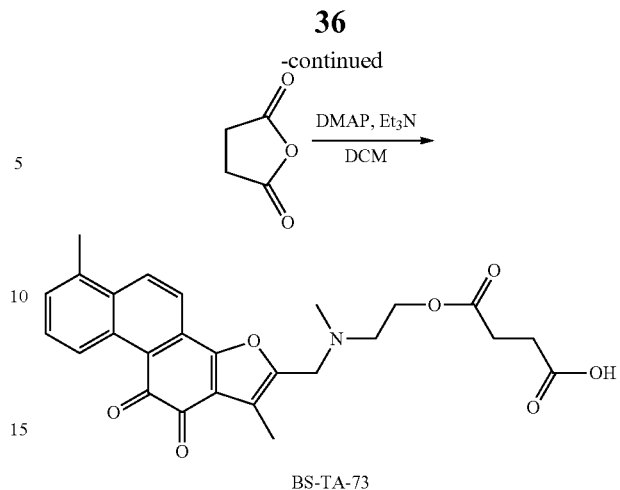

BS-TA-73 wherein, DMAP represents 4-dimethylaminopyridine.

To dichloromethane (8 mL) are added BS-TA-B17 (200 mg, 0.550 mmol), 4-dimethylaminopyridine (6.7 mg, 0.0550 mmol) and triethylamine (56 mg, 0.550 mmol), followed by succinic anhydride (66 mg, 0.660 mmol). The reaction solution is stirred for 1 hour at room temperature. Once the reaction completes, the resulted solid is filtered. The crude product resulted is separated and purified via preparative chromatography to give the compound BS-TA-73 (25 mg, yield 9.8%) as a brown solid.

LC-MS: retention time: 1.5 min (97.56%); m/z: 464.0 (M+H).

$^1$H NMR (400 Hz, DMSO d-$_6$) δ 9.14 (d, J=8.0 Hz, 1H), 8.42 (d, J=8.0 Hz, 1H), 7.83 (t, 1H), 7.59 (t, 1H), 7.42 (d, J=6.4 Hz, 1H), 4.76 (t, 2H), 3.67 (d, J=7.2 Hz, 2H), 2.70-2.64 (m, 5H), 2.48-2.40 (m, 4H), 2.27 (s, 3H), 2.20 (s, 3H).

EXAMPLE 10

Synthesis of Compound BS-TA-79

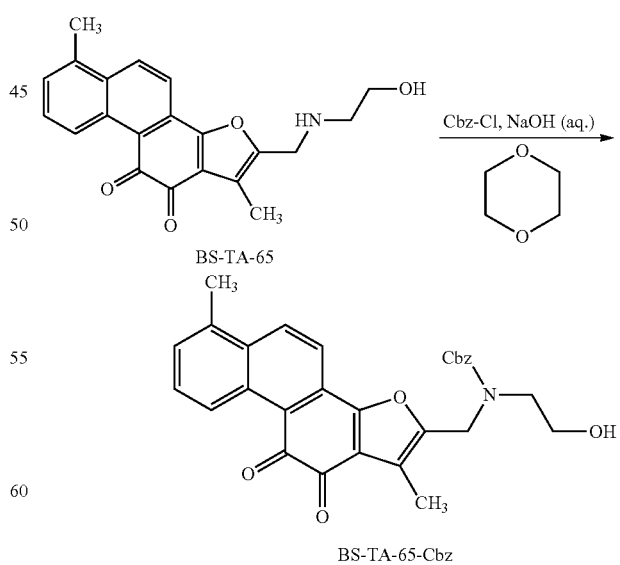

BS-TA-65

BS-TA-65-Cbz wherein, Cbz-Cl represents phenylmethyl chloroformate.

1M sodium hydroxide solution is added to a dioxane (120 mL) suspension of BS-TA-65 (6.0 g, 17.14 mmol) in an ice bath, followed by the dropwise addition of benzyl chloroformate (8.5 g, 34.28 mmol) and allowed to react for 3 hours with stirring at 0° C. Once the reaction completes, water is added and to the reaction solution and ethyl acetate (50 mL*2) is used for extraction.

The organic phase is washed with saturated sodium bicarbonate solution, dried, and concentrated to give the compound BS-TA-65-Cbz (6.2 g, 74.7%).

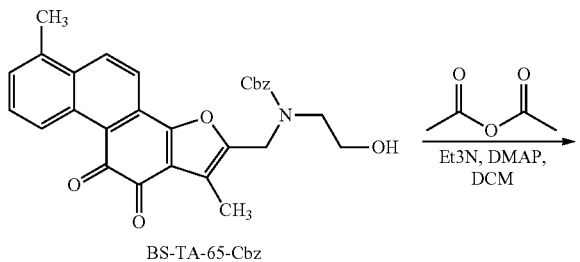

BS-TA-65-Cbz

To dichloromethane (100 mL) are added BS-TA-65-Cbz (6.2 g, 12.84 mmol), triethylamine (1.7 g, 14.12 mmol) and 4-dimethylaminopyridine (129.5 mg, 0.1284 mmol), followed by acetic anhydride (2.6 g, 25.68 mmol) under an ice bath. After the reaction solution is stirred for 30 minutes, water is added and dichloromethane (50 mL*2) is used for extraction. After drying and concentrating, the crude product BS-TA-79-Cbz (5.4 g, 80.1%) is obtained, which is directly applied to the next step of reaction without purification.

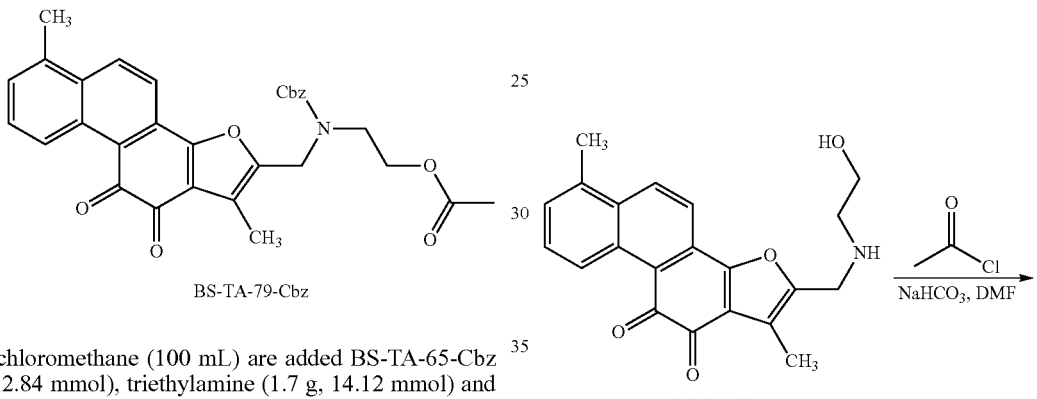

BS-TA-79-Cbz

BS-TA-79

Pd/C (1.0 g) is added to a methanol solution (160 mL) of BS-TA-79-Cbz (5.4 g, 10.29 mmol). The reaction solution is displaced with hydrogen 3 times and stirred for 4 hours under hydrogen at normal temperature. Once the reaction completes, the reaction solution is filtered. The crude product resulted from concentrating the filtrate is purified and separated via preparative thin layer chromatography (dichloromethane/ethyl acetate 1:1) to give the compound BS-TA-79 (1.3 mg, yield 11.1%) as a brown solid.

LC-MS: retention time: 3.56 min (85.62%), m/z: 392.0 (M+H).

$^1$H NMR (400 Hz, CDCl$_3$) δ 9.26 (d, J=8.8 Hz, 1H), 8.31 (d, J=8.8 Hz, 1H), 7.86 (d, J=8.8 Hz, 1H), 7.57 (t, 1H), 7.36 (d, J=6.8 Hz, 1H), 4.24 (t, J=5.2 Hz, 2H), 3.92 (s, 2H), 2.97 (t, J=5.6 Hz, 2H), 2.71 (s, 3H), 2.30 (s, 3H), 2.09 (s, 3H).

EXAMPLE 11

Synthesis of Compound BS-TA-80

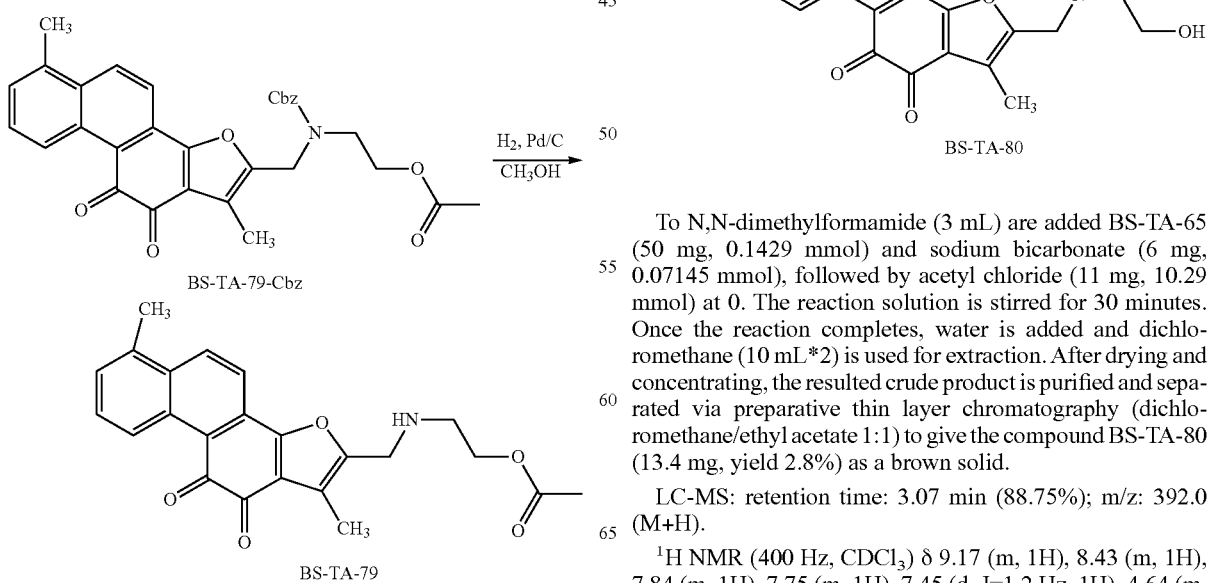

BS-TA-65

BS-TA-80

To N,N-dimethylformamide (3 mL) are added BS-TA-65 (50 mg, 0.1429 mmol) and sodium bicarbonate (6 mg, 0.07145 mmol), followed by acetyl chloride (11 mg, 10.29 mmol) at 0. The reaction solution is stirred for 30 minutes. Once the reaction completes, water is added and dichloromethane (10 mL*2) is used for extraction. After drying and concentrating, the resulted crude product is purified and separated via preparative thin layer chromatography (dichloromethane/ethyl acetate 1:1) to give the compound BS-TA-80 (13.4 mg, yield 2.8%) as a brown solid.

LC-MS: retention time: 3.07 min (88.75%); m/z: 392.0 (M+H).

$^1$H NMR (400 Hz, CDCl$_3$) δ 9.17 (m, 1H), 8.43 (m, 1H), 7.84 (m, 1H), 7.75 (m, 1H), 7.45 (d, J=1.2 Hz, 1H), 4.64 (m,

2H), 3.64 (t, J=6.0 Hz, 2H), 3.47 (t, J=5.6 Hz, 2H), 3.08 (t, J=6.0 Hz, 1H), 2.08 (s, 3H), 2.25 (s, 3H), 2.10-1.79 (m, 3H).

EXAMPLE 12

Synthesis of Compound BS-TA-81

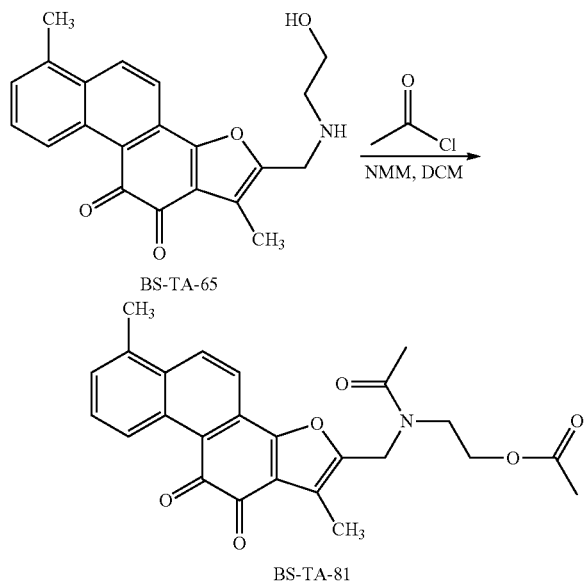

wherein, NMM represents N-methylmorpholine.

To dichloromethane (5 mL) are added BS-TA-65 (50 mg, 0.1429 mmol) and N-methylmorpholine (7 mg, 0.1429 mmol), followed by acetyl chloride (11 mg, 0.1429 mmol) at 0. The reaction solution is stirred for 30 minutes. Once the reaction completes, water is added and dichloromethane (10 mL*2) is used for extraction. After drying and concentrating the organic phase, the resulted crude product is purified and separated via preparative thin layer chromatography (dichloromethane/ethyl acetate 1:1) to give the compound BS-TA-81 (11.6 mg, 18.7%) as a brown solid.

LC-MS: retention time: 3.49 min (92.16%), m/z: 433.8 (M+H).

$^1$H NMR (400 Hz, CDCl$_3$) δ 9.27 (m, 1H), 8.33 (m, 1H), 7.80 (m, 1H), 7.57 (m, 1H), 7.36 (d, J=8.0 Hz, 1H), 4.69 (s, 1H), 4.60 (s, 1H), 4.30 (m, 2H), 2.71 (d, J=4.4 Hz, 3H), 2.37-2.08 (m, 9H).

EXAMPLE 13

Evaluation of the 2-Aminated Methylene or 2-Esterified Methylene Tanshinone I Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), and Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection (CCTCC).

Reagents: The standard sample of tanshinone I (TA) is purchased from Chengdu Mansite Pharmaceutical Co., Ltd., Sichuan, China; the 2-aminated methylene or 2-esterified methylene tanshinone I derivatives are prepared according to the present invention.

Main apparatuses: a cell incubator (model: Thermo Scientific 3111) and a microplate absorbance reader (model: Bio-Rad iMark).

(2) Experimental Method

The standard sample of tanshinone I (TA) and the 2-aminated methylene or 2-esterified methylene tanshinone I derivatives of the present invention are sufficiently dissolved with dimethylsulfoxide to produce a stock solution of 10 mg/mL, which is refrigerated at 4° C. and stored in dark, and is diluted with a cell culture medium to the desired concentration prior to experimentation.

Obtaining 6000 well-growing leukemia cells and inoculating them into wells of a 96-well cell culture plate. The culture medium is the RPMI-1640 cell culture medium containing 10% fetal bovine serum. After adding on the second day the 2-aminated methylene or 2-esterified methylene tanshinone I derivatives of different concentrations and mixing uniformly, placing the plate in a carbon dioxide cell incubator (5% CO$_2$) at 37° C. and incubated for 72 hours. Then the viable cell concentration is determined by MTT method. In this experiment, the cell viability in control group (not treated with any compound) is set as 100%, and the cell viability (%) after treatment by the compounds and the half maximum inhibitory concentration for the leukemia cell at 72 hours (IC$_{50}$ value of 72 hours, μg/mL) are calculated.

(3) The Experimental Results

The experimental results are shown in table 1.

Table 1 shows that the 2-aminated methylene or 2-esterified methylene tanshinone I derivatives of the present invention can induce the death of human chronic myeloid leukemia cells, acute myeloid leukemia cells and acute lymphocytic leukemia cells, and inhibit the growth of these leukemia cells. This is especially obvious for the compound BS-TA-65, which exhibits broad-spectrum antitumor activity for all the cell lines in this experiment. In particular, as compared with tanshinone I per se, the compound BS-TA-65 improves the anti-H9 (acute lymphoblastic leukemia) and anti-NB4 (acute promyelocytic leukemia) cell lines activity by 27-fold and 24-fold, respectively. BS-TA-71 improves the anti-H9 (acute lymphoblastic leukemia) activity by 28-fold. In addition, BS-TA-B17 improves the anti-Jurkat (acute lymphoblastic leukemia) activity by more than 10-fold.

TABLE 1

Determination of the inhibitory concentrations of the 2-aminated methylene or 2-esterified methylene tanshinone I derivatives for leukemia cell growth (72 h, IC$_{50}$ (μg/mL) value and IC$_{90}$ (μg/mL) value).

| Compounds | K562/ADR | | Kasumi-1 | | NB4 | |
| --- | --- | --- | --- | --- | --- | --- |
| | IC$_{50}$ | IC$_{90}$ | IC$_{50}$ | IC$_{90}$ | IC$_{50}$ | IC$_{90}$ |
| TA | 0.88 | 4.17 | 0.99 | 3.62 | 0.98 | 2.50 |
| BS-TA-A01 | 2.33 | 6.24 | 1.75 | 3.91 | 0.99 | 3.97 |
| BS-TA-A03 | 2.3 | 6.61 | 2.35 | 7.79 | 1.93 | 9.65 |
| BS-TA-B01 | 1.13 | 2.95 | 0.66 | 1.91 | 0.26 | 0.96 |
| BS-TA-B03 | 1.22 | 2.69 | 0.81 | 2 | 0.92 | 3.01 |
| BS-TA-B06 | 0.81 | 1.8 | 0.57 | 1.73 | 2.13 | 7.29 |
| BS-TA-B07 | 3.22 | 6.38 | 1.07 | 3.86 | 1.35 | 3.74 |
| BS-TA-B10 | 0.76 | 1.8 | 0.4 | 0.92 | 5.79 | 15.42 |
| BS-TA-B12 | 1.5 | 2.79 | 0.89 | 1.9 | 0.94 | 1.9 |
| BS-TA-B14 | 0.77 | 1.82 | 0.6 | 1.99 | 3.59 | 13.71 |
| BS-TA-B17 | 0.31 | 0.86 | 0.12 | 0.23 | 0.14 | 0.41 |

TABLE 1-continued

Determination of the inhibitory concentrations of the
2-aminated methylene or 2-esterified methylene tanshinone
I derivatives for leukemia cell growth (72 h, $IC_{50}$ (μg/mL)
value and $IC_{90}$ (μg/mL) value).

| | | | | | | |
|---|---|---|---|---|---|---|
| BS-TA-B21 | 1.3 | 2.73 | 0.83 | 1.8 | 1.53 | 5.46 |
| BS-TA-50 | 11.22 | >16 | 5.03 | >16 | 0.99 | 7 |
| BS-TA-60 | 1.36 | 5.12 | 1.61 | 3.86 | 0.9 | 2.98 |
| BS-TA-61 | 0.61 | 1.61 | 0.31 | 1.28 | 0.73 | 1.9 |
| BS-TA-62 | 0.78 | 3.48 | 0.42 | 0.97 | 1.42 | 3.85 |
| BS-TA-63 | 1.26 | 4.6 | 1.48 | 3.89 | 3.73 | 10.37 |
| BS-TA-64 | 0.84 | 2.82 | 0.33 | 0.7 | 0.25 | 0.87 |
| BS-TA-65 | 0.16 | 1.08 | 0.074 | 0.12 | 0.04 | 0.08 |
| BS-TA-71 | 0.47 | 0.76 | 0.13 | 0.39 | 0.15 | 0.41 |
| BS-TA-72 | 1.5 | 2 | 0.28 | 0.47 | 0.35 | 0.71 |
| BS-TA-73 | 1.38 | 2.74 | 0.27 | 0.73 | 0.21 | 0.68 |
| BS-TA-74 | 0.8 | 1.8 | 0.26 | 1.57 | 0.19 | 0.49 |

| Compounds | H9 | | Jurkat | |
|---|---|---|---|---|
| | $IC_{50}$ | $IC_{90}$ | $IC_{50}$ | $IC_{90}$ |
| TA | 3.5 | 13.06 | 1.74 | 8.42 |
| BS-TA-A01 | 3.09 | 10.36 | 3 | 9.27 |
| BS-TA-A03 | 6.4 | >16 | 5.54 | 17.05 |
| BS-TA-B01 | 0.7 | 2.3 | 0.96 | 5.3 |
| BS-TA-B03 | 3.3 | 6.8 | 2.36 | 6.15 |
| BS-TA-B06 | 3.2 | 14.1 | 5.25 | 16 |
| BS-TA-B07 | 2.9 | 7.5 | 3.11 | 9.52 |
| BS-TA-B10 | 6 | >16 | >16 | >16 |
| BS-TA-B12 | 4.11 | 10.5 | 1.78 | 5.91 |
| BS-TA-B14 | 2 | 11.9 | 6.66 | >16 |
| BS-TA-B17 | 0.45 | 0.96 | 0.16 | 0.36 |
| BS-TA-B21 | 2.2 | 5.9 | 3.41 | 9.55 |
| BS-TA-50 | 6.25 | 15.86 | 4.79 | >16 |
| BS-TA-60 | 1.4 | 4 | 1.28 | 3.99 |
| BS-TA-61 | 0.57 | 0.9 | 0.56 | 0.99 |
| BS-TA-62 | 0.6 | 1.8 | 0.89 | 3.47 |
| BS-TA-63 | 3.75 | 15.33 | 3 | 7.56 |
| BS-TA-64 | 0.59 | 1.63 | 0.54 | 1.92 |
| BS-TA-65 | 0.13 | 0.41 | 0.17 | 0.47 |
| BS-TA-71 | 0.125 | 0.49 | 0.37 | 0.94 |
| BS-TA-72 | 0.45 | 1.6 | 0.31 | 0.99 |
| BS-TA-73 | 0.19 | 0.97 | 0.98 | 3.4 |
| BS-TA-74 | 0.25 | 1.49 | 0.96 | 1.86 |

EXAMPLE 14

Evaluation of the Anti-Human Multiple Myeloma Cell Activities by the 2-Aminated Methylene or 2-Esterified Methylene Tanshinone I Derivatives of the Present Invention (1) Experimental Materials Myeloma cell lines: RPMI8226 (multiple myeloma), purchased from Fuxiang Bio-tech Co. Ltd., Shanghai, China.

Reagents: the same as in Example 13.

Main apparatuses: cell incubator (model: Thermo Scientific 3111) and a microplate absorbance reader (model: Bio-Rad iMark).

(2) Experimental Method

The standard sample of tanshinone I (TA) and the 2-aminated methylene or 2-esterified methylene tanshinone I derivatives of the present invention are sufficiently dissolved with dimethylsulfoxide to produce a stock solution of 10 mg/mL, which is refrigerated at 4° C. and stored in dark, and is diluted with a cell culture medium to the desired concentration prior to experimentation.

Obtaining 6000 well-growing myeloma cells as above and inoculating them into wells of a 96-well cell culture plate. The culture medium is the 1640 cell culture medium containing 10% fetal bovine serum. After adding the 2-aminated methylene or 2-esterified methylene tanshinone I derivatives of different concentrations and mixing uniformly, placing the plate in a carbon dioxide cell incubator (5% $CO_2$) at 37° C. and incubated for 72 hours. Then the viable cell concentration is determined by MTT method. In this experiment, the cell viability in control group (not treated with any compound) is set as 100%, and the cell viability (%) after treatment by the compounds and the half maximum inhibitory concentration for the leukemia cell at 72 hours ($IC_{50}$ value of 72 hours, μg/mL) are calculated.

(3) The Experimental Results

The experimental results are shown in table 2.

Table 2 shows that the 2-aminated methylene or 2-esterified methylene tanshinone I derivatives of the present invention can induce the death of human myeloma cells and inhibit the growth of the tumor cells. As compared with tanshinone I per se, the 2-aminated methylene or 2-esterified methylene tanshinone I derivatives of the present invention BS-TA-65 and BS-TA-72 improve the inhibition of the RPMI8226 cell line by more than 7-fold.

EXAMPLE 15

Evaluation of Anti-Human Solid Tumor Effect of the 2-Aminated Methylene or 2-Esterified Methylene Tanshinone I Derivatives of the Present Invention (1) Experimental Materials Human solid tumor cell lines:

Hep-2 (laryngeal carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Hep G2 (human liver cancer cell), Becap37 (human breast cancer cell) and Hela (human cervical cancer cell), all of which are donated by Cancer Research Institute of Zhejiang University, China.

Reagents: the same as in Example 13.

Main apparatuses: cell incubator (model: Thermo Scientific 3111) and a microplate absorbance reader (model: Bio-Rad iMark).

(2) Experimental Method

The standard sample of tanshinone I (TA) and the 2-aminated methylene or 2-esterified methylene tanshinone I derivatives of the present invention are sufficiently dissolved with dimethylsulfoxide to produce a stock solution of 10 mg/mL, which is refrigerated at 4° C. and stored in dark, and is diluted with a cell culture medium to the desired concentration prior to experimentation.

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. and incubated for 24 hours. After adding the 2-aminated methylene or 2-esterified methylene tanshinone I derivatives of different concentrations and mixing uniformly, the plate is placed in a carbon dioxide cell incubator (5% $CO_2$) at 37° C. and incubated for 72 hours. Then the viable cell concentration is determined by the MTT method. In this experiment, the cell viability in control group (not treated with any compound) is set as 100%, and the cell viability (%) after treatment by the compounds and the half maximum inhibitory concentration for the leukemia cell at 72 hours ($IC_{50}$ value of 72 hours, μg/mL) are calculated. P(3) Experimental Results PThe experimental results are shown in Table 2. PTable 2 shows that the 2-aminated methylene or 2-esterified methylene tanshinone I derivatives of the present invention can induce the death of human solid tumor cells and inhibit the growth of these tumor cells. As compared with tanshinone I per se, the 2-aminated methylene or 2-esterified methylene tanshinone I derivatives of the present invention show significantly improved anti-solid tumor cells activity. Specifically, BS-TA-65 exhibits broad-spectrum antitumor activity for all the cell lines tested in this experiment. In particular, the compound improves the anti-U87 MG (malignant glioma cell) activity by more than 42-fold. In addition, the compounds BS-TA-71, BS-TA-B03 and BS-TA-B17 improve the anti-A549 (human lung cancer) activity by more than 4-fold; the compound BS-TA-B17 improve the anti-PANC-1 (pancreatic cancer) and anti-CaES-17 (esophageal cancer cell) activity by more than 10-fold and 7-fold, respectively. BS-TA-71, BS-TA-72 and BS-TA-B17 improve the anti-Hep-G2 (human liver cancer cell) activity by more than 3-fold. BS-TA-71 and BS-TA-B01 improve the anti-Becap37 (human breast cancer cell) activity by more than 7-fold. The compound BS-TA-71 improves the anti-Hep-2 (laryngeal carcinoma) activity by more than 4-fold. BS-TA-B01 improves the anti-MG63 (osteosarcoma) activity by almost 3-fold. BS-TA-71 improves the anti-Hela (human cervical cancer cell) activity by more than 8-fold. BS-TA-71 and BA-TA-B12 improve the anti-CNE (nasopharyngeal carcinoma cell) activity by more than 11-fold. P

TABLE 2

Determination of the inhibitory concentrations of the 2-aminated methylene or 2-esterified methylene tanshinone I derivatives on multiple myeloma and human solid tumor cell growth (72 h, $IC_{50}$ value and $IC_{90}$ value, μg/mL).

| Compounds | RPMI 8226 | | A549 | | PANC-1 | |
|---|---|---|---|---|---|---|
| | $IC_{50}$ | $IC_{90}$ | $IC_{50}$ | $IC_{90}$ | $IC_{50}$ | $IC_{90}$ |
| TA | 0.96 | 10.86 | 4.03 | 17.29 | 2.7 | >16 |
| BS-TA-A01 | 3.39 | 7.85 | 6.23 | >16 | 3.31 | 12.03 |
| BS-TA-A03 | 8.4 | >16 | 10.56 | 24.23 | 3.08 | 13.34 |
| BS-TA-B01 | 0.52 | 2.9 | 1.7 | 17 | 0.81 | 16 |
| BS-TA-B03 | 2.83 | 5.87 | 0.8 | 4.43 | 3.14 | 16 |
| BS-TA-B06 | 6.16 | 16 | 1.59 | 10 | 1.57 | 16.72 |
| BS-TA-B07 | 3.46 | 10.16 | 5.98 | 21.95 | 1.33 | 8.21 |
| BS-TA-B10 | 15.82 | >16 | 1.28 | 6 | 0.88 | 5.82 |
| BS-TA-B12 | 3.72 | 7.13 | 1.65 | 4.33 | 1.06 | 4.16 |
| BS-TA-B14 | 8 | >16 | 1.75 | 9 | 1.88 | 6.19 |
| BS-TA-B17 | 0.39 | 0.8 | 0.83 | 3.13 | 0.27 | 2.6 |
| BS-TA-B21 | 5.78 | 10.47 | 1.8 | 10 | 1.14 | 7.28 |
| BS-TA-50 | 3.86 | 16 | 8.9 | >16 | 4.24 | >16 |
| BS-TA-60 | 2 | 7.64 | 3.78 | 9.78 | 1.74 | 3.58 |
| BS-TA-61 | 1.82 | 3.92 | 2.76 | 6.41 | 0.74 | 4.95 |
| BS-TA-62 | 2.64 | 7.68 | 3.3 | 21.35 | 1.42 | 16 |
| BS-TA-63 | 7.76 | 16 | 6.5 | 23.4 | 4.92 | 20.86 |
| BS-TA-64 | 0.4 | 0.92 | 1.4 | 4.46 | 0.71 | 5.07 |
| BS-TA-65 | 0.125 | 0.25 | 0.979 | 3.52 | 0.26 | 1.9 |
| BS-TA-71 | 0.25 | 0.83 | 0.8 | 2.82 | 0.4 | 4.73 |
| BS-TA-72 | 0.12 | 0.87 | 1.07 | 3.7 | 0.75 | 8.96 |
| BS-TA-73 | 0.38 | 1.55 | 1.72 | 4.79 | 1.07 | 5 |
| BS-TA-74 | 0.45 | 1.78 | 1.79 | 6.05 | 0.87 | 11.09 |

| Compounds | Becap-37 | | MG-63 | | Hep G2 | | RKO | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 3.03 | >16 | 0.96 | >16 | 2.19 | 22.13 | 1.83 | >16 |
| BS-TA-A01 | 4.74 | 10.76 | 2.87 | 13.99 | 4.82 | 16 | 1.46 | 13.44 |
| BS-TA-A03 | 14.24 | >16 | 4.86 | >16 | 10.59 | >16 | 2.77 | >16 |
| BS-TA-B01 | 0.43 | 3.73 | 0.38 | 14.93 | 1.25 | 9.41 | 0.17 | 16 |
| BS-TA-B03 | 4 | 9.37 | 4.53 | 12.99 | 4.69 | 22.11 | 0.49 | 14.56 |
| BS-TA-B06 | 5.9 | >16 | 4.76 | >16 | 13.51 | >16 | 3.42 | >16 |
| BS-TA-B07 | 5.23 | 14.34 | 8.14 | >16 | 8.46 | >16 | 0.93 | 17.04 |
| BS-TA-B10 | >16 | >16 | >16 | >16 | >16 | >16 | 5.47 | >16 |
| BS-TA-B12 | 3.34 | 7.38 | 3.37 | 5.49 | 3.8 | 7.96 | 0.7 | 5.26 |
| BS-TA-B14 | 4.6 | >16 | 4.86 | >16 | 16 | >16 | 3.36 | >16 |
| BS-TA-B17 | 0.76 | 1.77 | 0.78 | 1.76 | 0.56 | 1.82 | 0.125 | 1.3 |
| BS-TA-B21 | 6.73 | 15.08 | 4.68 | 15.31 | 7.3 | 25.75 | 2.46 | 27.85 |
| BS-TA-50 | 8.1 | >16 | 1.67 | >16 | >16 | >16 | 2.5 | >16 |
| BS-TA-60 | 1.88 | 3.67 | 1.24 | 5.23 | 2.5 | 5.97 | 0.52 | 1.88 |
| BS-TA-61 | 2.54 | 4.92 | 2.34 | 6.79 | 2.95 | 9.75 | 0.46 | 6.98 |
| BS-TA-62 | 5.04 | 11.64 | 4.88 | >16 | 5.41 | 22.56 | 0.47 | >16 |
| BS-TA-63 | 16 | >16 | 14.13 | >16 | 15.65 | >16 | 1.86 | 17.63 |
| BS-TA-64 | 0.77 | 1.67 | 0.82 | 2.16 | 1.31 | 3.66 | 0.29 | 5.56 |
| BS-TA-65 | 0.27 | 0.68 | 0.31 | 0.98 | 0.31 | 1.5 | 0.037 | 0.29 |
| BS-TA-71 | 0.4 | 0.9 | 0.61 | 1.79 | 0.66 | 1.85 | 0.14 | 1.28 |
| BS-TA-72 | 1.02 | 1.94 | 1.08 | 2.56 | 0.71 | 3.85 | 0.25 | 2.38 |
| BS-TA-73 | 1.06 | 1.91 | 1.01 | 3.71 | 1.39 | 4.64 | 0.2 | 0.87 |
| BS-TA-74 | 0.85 | 1.81 | 1.02 | 3.26 | 1.35 | 5.26 | 0.28 | 2.88 |

TABLE 2-continued

Determination of the inhibitory concentrations of the 2-aminated methylene or 2-esterified methylene tanshinone I derivatives on multiple myeloma and human solid tumor cell growth (72 h, $IC_{50}$ value and $IC_{90}$ value, μg/mL).

| Compounds | U87-MG | | Hela | | CaEs-17 | | CNE | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 6.36 | 14.63 | 4 | >16 | 3.18 | 16.00 | 7.4 | >16 |
| BS-TA-A01 | 5.71 | 14.15 | 4.5 | 14.86 | 6.36 | 12.67 | 4.1 | 45 |
| BS-TA-A03 | >16 | >16 | 5 | >16 | 15.48 | >16 | 8.5 | >16 |
| BS-TA-B01 | 0.74 | 8 | 1.31 | 16.22 | 0.97 | 3.81 | 0.817 | 39 |
| BS-TA-B03 | 2.36 | 3.85 | 3.99 | 10.96 | 5.55 | 10.35 | 8.8 | 43.58 |
| BS-TA-B06 | 6.5 | >16 | 7.49 | >16 | 19.26 | >16 | 11.787 | >16 |
| BS-TA-B07 | 10.07 | 21.22 | 6.86 | 18.47 | 9.16 | 19.68 | 9 | >16 |
| BS-TA-B10 | >16 | >16 | 15.55 | >16 | >16 | >16 | >16 | >16 |
| BS-TA-B12 | 1.16 | 3.4 | 1.46 | 3.58 | 0.73 | 1.97 | 0.45 | 0.62 |
| BS-TA-B14 | 3.85 | >16 | 5.28 | 84.2 | >16 | >16 | >16 | >16 |
| BS-TA-B17 | 0.76 | 1.82 | 0.67 | 1.8 | 0.45 | 0.91 | 1.4 | 3 |
| BS-TA-B21 | 6.79 | 21.32 | 3.3 | 7.9 | 8.71 | 14.24 | 5.99 | 79 |
| BS-TA-50 | 4.67 | >16 | 7.78 | >16 | 8.45 | >16 | 3.87 | >16 |
| BS-TA-60 | 0.36 | 18.8 | 3.32 | 7.35 | 3.58 | 7.74 | 3.2 | 7.2 |
| BS-TA-61 | 2.59 | 3.87 | 1.49 | 4 | 3 | 5.07 | 2.8 | 7.2 |
| BS-TA-62 | 3.2 | 7.65 | 9.26 | >16 | 6.33 | 11.82 | 1.8 | 18 |
| BS-TA-63 | 15.83 | >16 | 8.77 | >16 | >16 | >16 | >16 | >16 |
| BS-TA-64 | 1.16 | 3.72 | 2.16 | 3.9 | 0.88 | 1.85 | 1.8 | 3.8 |
| BS-TA-65 | 0.15 | 0.35 | 0.42 | 1 | 0.3 | 0.81 | 0.6 | 1.8 |
| BS-TA-71 | 0.66 | 1.55 | 0.47 | 1.75 | 0.52 | 0.59 | 0.63 | 1.43 |
| BS-TA-72 | 1.46 | 3.65 | 0.89 | 1.84 | 1.84 | 3.98 | 2.02 | 3.61 |
| BS-TA-73 | 1.19 | 3.44 | 1 | 3.81 | 1.14 | 1.86 | 1.38 | 3.7 |
| BS-TA-74 | 0.86 | 1.83 | 1.15 | 3.59 | 1.09 | 1.86 | 1.39 | 2.91 |

| Compounds | HeP-2 | | MGC-803 | | PC-3 | | SK-OV-3 | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 3.15 | >16 | 1.62 | 9.26 | 6.63 | 10.57 | >16 | >16 |
| BS-TA-A01 | 3.96 | 19.12 | 5.38 | 16 | 5.32 | 12.57 | >16 | >16 |
| BS-TA-A03 | 6.82 | >16 | 9.22 | 23.25 | 14.43 | >16 | >16 | >16 |
| BS-TA-B01 | 0.88 | 29.59 | 0.79 | 7.25 | 1.83 | 16 | 5.41 | 22.83 |
| BS-TA-B03 | 6.11 | 18.46 | 3.86 | 7.99 | 5.39 | 12.34 | 12.83 | 21.68 |
| BS-TA-B06 | 9.23 | >16 | 7.82 | >16 | 10.34 | 24.47 | >16 | >16 |
| BS-TA-B07 | 9.45 | >16 | 6.9 | 17.14 | 7.05 | 16 | >16 | >16 |
| BS-TA-B10 | 15.77 | >16 | >16 | >16 | >16 | >16 | >16 | >16 |
| BS-TA-B12 | 4.01 | 9.08 | 2.48 | 5.05 | 9.3 | 11.18 | 2.53 | 3.84 |
| BS-TA-B14 | 14.31 | 35.23 | 14.42 | >16 | 14.66 | >16 | >16 | >16 |
| BS-TA-B17 | 0.87 | 2.79 | 0.37 | 2.94 | 0.63 | 2 | 1.44 | 1.97 |
| BS-TA-B21 | 5.16 | 23.69 | 7.01 | 17.29 | 7.3 | 15.1 | >16 | >16 |
| BS-TA-50 | 13.72 | >16 | 8.91 | >16 | 10.72 | >16 | >16 | >16 |
| BS-TA-60 | 1.79 | 7.41 | 2.9 | 5.4 | 5.03 | 10.77 | 9.78 | 22.66 |
| BS-TA-61 | 0.84 | 2.52 | 2.47 | 8.33 | 2.65 | 6.49 | 5.83 | 9.47 |
| BS-TA-62 | 6.81 | >16 | 6.3 | 14.07 | 3.21 | 8.76 | >16 | >16 |
| BS-TA-63 | 3.39 | 22.43 | 14.86 | >16 | 5.83 | 18.88 | >16 | >16 |
| BS-TA-64 | 1.67 | 3.65 | 0.85 | 3.24 | 1.8 | 4.15 | 3.55 | 7.76 |
| BS-TA-65 | 0.78 | 2.38 | 0.15 | 1.7 | 0.44 | 3.58 | 0.86 | 1.91 |
| BS-TA-71 | 0.62 | 1.76 | 0.41 | 2.24 | 0.92 | 3.74 | 1.66 | 3.39 |
| BS-TA-72 | 1.59 | 3.77 | 1.5 | 9.94 | 1.68 | 9.92 | 5.91 | 10.94 |
| BS-TA-73 | 0.81 | 3.21 | 0.84 | 4.9 | 1.73 | 7.04 | 3.54 | 7.27 |
| BS-TA-74 | 1.28 | 3.67 | 0.8 | 3.87 | 1.71 | 8.19 | 3.96 | 7.99 |

The invention claimed is:

1. A 2-aminated methylene or 2-esterified methylene tanshinone I derivative of formula (I), or a pharmaceutically acceptable salt thereof,

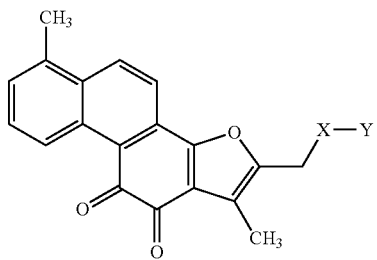

I

X is nitrogen or oxygen;

when X is nitrogen, Y is ($R_1R_2$), then the compound of formula (I) is 2-aminated methylene tanshinone I of formula I-1; and when X is oxygen, Y is —(CO)R, then the compound of formula (I) is 2-esterified methylene tanshinone I of formula I-2,

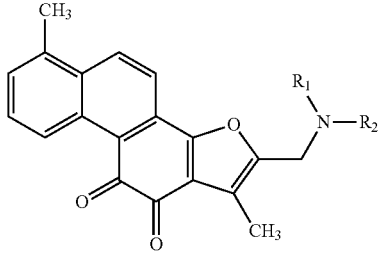

I-1

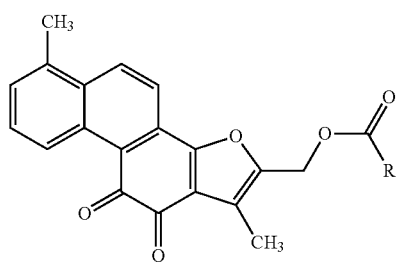

I-2 wherein
R is selected from the group consisting of H, substituted or unsubstituted $C_2$-$C_{18}$ alkyl, substituted or unsubstituted $C_2$-$C_{18}$ alkenyl or alkynyl, substituted or unsubstituted $C_3$-$C_7$ cycloalkyl or cycloalkenyl, substituted or unsubstituted aryl, and substituted or unsubstituted heteroaryl or heterocyclyl;
$R_1$ is H, methyl or ethyl;
$R_2$ is $C_1$-$C_3$ alkyl substituted with a substituent selected from the group consisting of hydroxyl, $C_1$-$C_6$ alkylcarbonyloxy, cycloalkylcarbonyloxy, heterocyclyl carbonyloxy, amino-acid ester group wherein the amino is optionally substituted with $C_1$-$C_6$ alkoxycarbonyl, and $C_2$-$C_8$ dicarboxylic ester group optionally containing carbon-carbon double bond wherein one carboxyl is optionally esterified with $C_1$-$C_6$ alkyl; and
each of the aforementioned substituted group is optionally substituted by one or more substituents selected from the group consisting of halogen, nitro, cyano, amino, hydroxyl, thiol, carboxyl, $C_1$-$C_6$ substituted amino, $C_1$-$C_6$ alkoxy, and $C_1$-$C_6$ alkylthio.

2. The tanshinone I derivative or a pharmaceutically acceptable salt thereof according to claim 1, wherein X is nitrogen.

3. The tanshinone I derivative or a pharmaceutically acceptable salt thereof according to claim 1, wherein $R_1$ is H or methyl; $R_2$ is ethyl substituted with said substituent.

4. The tanshinone I derivative or a pharmaceutically acceptable salt thereof according to claim 1, wherein said substituent is selected from the group consisting of hydroxyl, acetoxy, propionyloxy, butyryloxy, isobutyryloxy, valeryloxy, isovaleryloxy, tert-valeryloxy, piperidylcarbonyloxy, piperazinylcarbonyloxy, morpholinylcarbonyloxy, pyrrolidylcarbonyloxy, imidazolidinylcarbonyloxy, glycine ester group, N-tert-butoxycarbonyl glycine ester group, valine ester group, glutamic acid ester group, lysine ester group, malonic acid monoester group, succinic acid monoester group, maleic acid monoester group, methyl maleic acid ester group, glutaric acid monoester group, adipic acid monoester group, and pimelic acid monoester group.

5. The tanshinone I derivative or a pharmaceutically acceptable salt thereof according to claim 2, which is quaternized by a benzyl optionally substituted with halogen on its phenyl ring.

6. The tanshinone I derivative or a pharmaceutically acceptable salt thereof according to claim 1, wherein X is oxygen or sulfur, and R is $C_2$-$C_6$ alkyl optionally substituted with hydroxyl or halogen, or is aryl or heteroaryl optionally substituted with hydroxyl or halogen.

7. The tanshinone I derivative or a pharmaceutically acceptable salt thereof according to claim 1, selected from the group consisting of the following compounds,

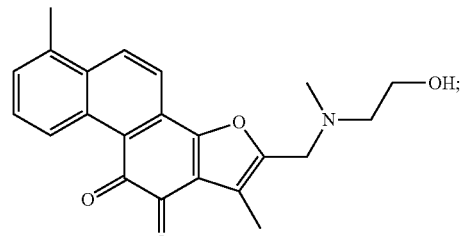

BS-TA-B17

2-(N-methylethanolamino)methyl-tanshinone I

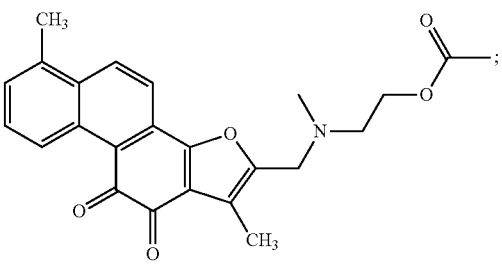

BS-TA-61

2-(N-methyl-acetoxyethyl-amino)methyl-tanshinone I

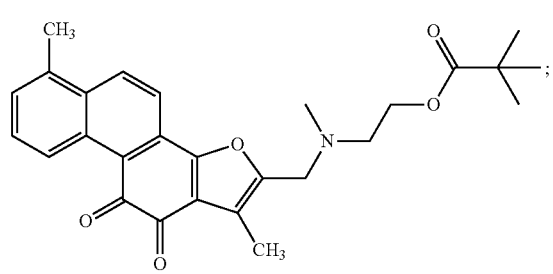

BS-TA-62

2-(N-methyl-t-butyryloxyethyl-amino)methyl-tanshinone I

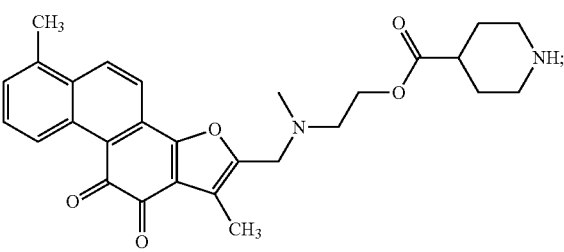

BS-TA-64

2-((N-methyl-(4-piperidylcarbonyl)oxyethyl-amino))methyl-tanshinone I

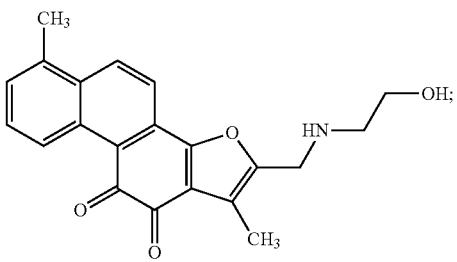

BS-TA-65

2-(ethanolamino)methyl-tanshinone I

-continued

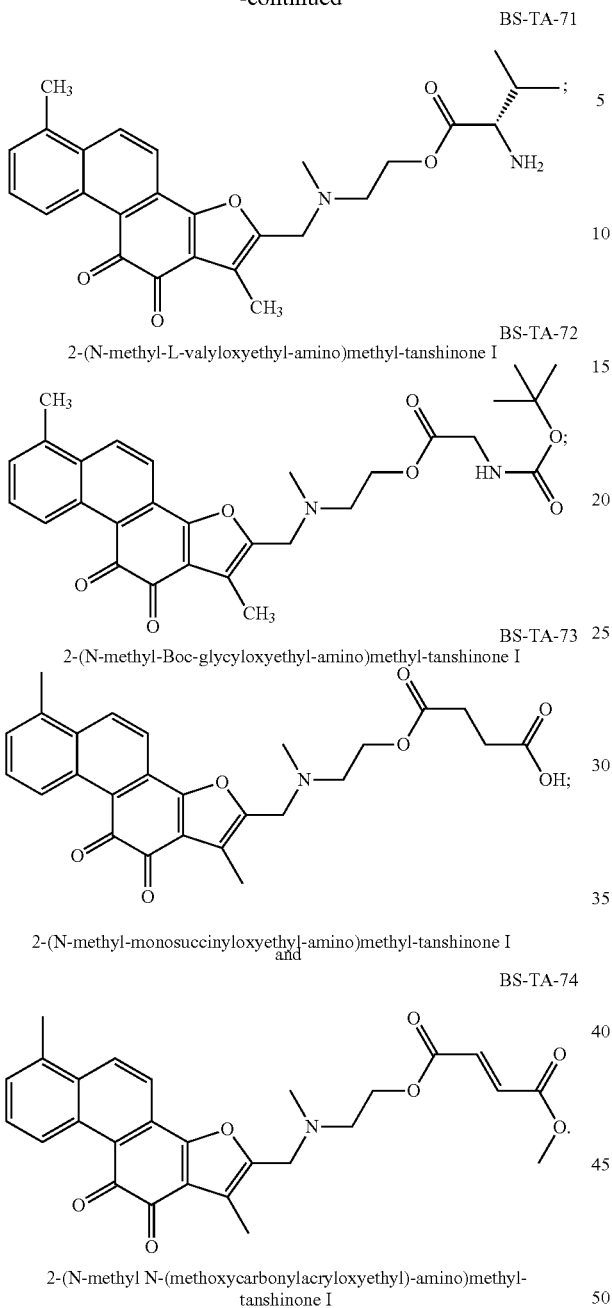

BS-TA-71
2-(N-methyl-L-valyloxyethyl-amino)methyl-tanshinone I

BS-TA-72
2-(N-methyl-Boc-glycyloxyethyl-amino)methyl-tanshinone I

BS-TA-73
2-(N-methyl-monosuccinyloxyethyl-amino)methyl-tanshinone I
and

BS-TA-74
2-(N-methyl N-(methoxycarbonylacryloxyethyl)-amino)methyl-tanshinone I

8. A process for preparing the compound of formula (I), comprising firstly subjecting tanshinone I (TA),

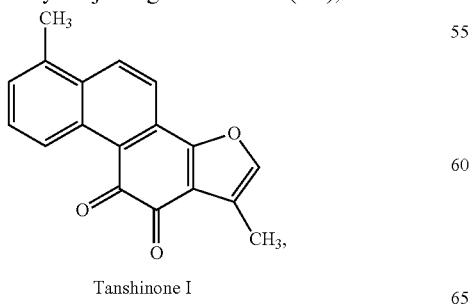

Tanshinone I to chloromethylation to produce a 2-chloromethyltanshinone I intermediate,

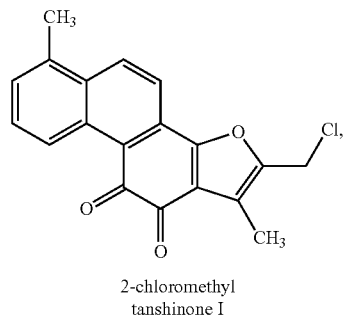 [SMILES: Cc1c(CCl)oc2c1C(=O)C(=O)c1c-2ccc2c(C)cccc12]

2-chloromethyl tanshinone I then reacting the resulted 2-chloromethyltanshinone I with a corresponding organic amine in the presence of an alkali to produce a 2-aminated methylene tanshinone I of formula (I-1),

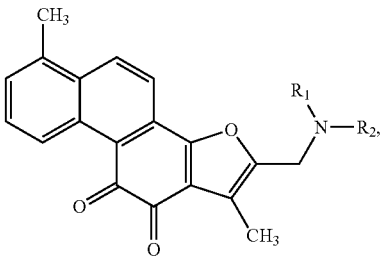

I-1 wherein $R_1$ and $R_2$ are as defined in formula (I-1) according to claim 1, and optionally further subjecting the resulted compound to derivatization to produce other compounds of formula (I); or
comprising firstly subjecting tanshinone I (TA),

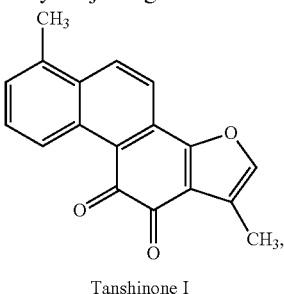

Tanshinone I to hydroxymethylation to produce a 2-hydroxymethyltanshinone I intermediate,

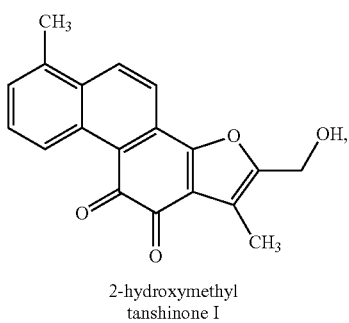 [SMILES: Cc1c(CO)oc2c1C(=O)C(=O)c1c-2ccc2c(C)cccc12]

2-hydroxymethyl tanshinone I then reacting the resulted 2-hydroxymethyltanshinone I with a corresponding organic acyl chloride or anhydride in the presence of an alkali to produce a 2-esterified methylene tanshinone I of formula (I-2),

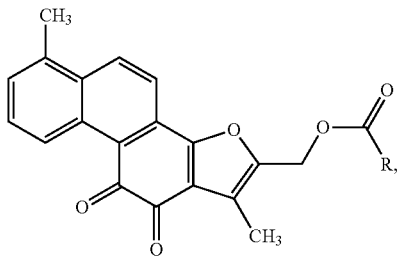

I-2 wherein R is as defined in formula (I-2) according to claim 1; and optionally further subjecting the resulted compound to derivatization to produce other compounds of formula (I).

9. A pharmaceutical composition, comprising the tanshinone I derivative or a pharmaceutically acceptable salt thereof according to claim 1 and optionally a pharmaceutically acceptable excipient.

10. A method for treating a subject suffering from tumor, comprising administrating to the subject in need thereof an effective amount of the tanshinone I derivative or a pharmaceutically acceptable salt thereof according to claim 1.

11. The method of claim 10, wherein the tumor is selected from leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma and prostate cancer.

12. The tanshinone I derivative of claim 1, wherein the tanshinone I derivative is

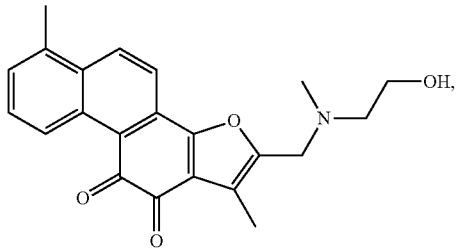 [SMILES: Cc1c(CN(C)CCO)oc2c1C(=O)C(=O)c1c-2ccc2c(C)cccc12]

or a pharmaceutically acceptable salt thereof.

* * * * *